United States Patent [19]

Greenlee et al.

[11] Patent Number: 5,348,955
[45] Date of Patent: Sep. 20, 1994

[54] N,N-DIACYLPIPERAZINES

[75] Inventors: William J. Greenlee, Teaneck; Mu T. Wu, Clark, both of N.J.

[73] Assignee: Merck & Co., Inc., Rahway, N.J.

[21] Appl. No.: 80,893

[22] Filed: Jun. 22, 1993

[51] Int. Cl.$^5$ .................. A61K 31/495; A61K 31/54; C07D 403/12; C07D 409/14
[52] U.S. Cl. .................. 514/227.8; 514/232.2; 514/235.8; 514/252; 514/255; 540/589; 544/60; 544/121; 544/357; 544/366; 544/379; 544/383; 544/388; 544/389; 544/390; 548/254; 548/334.1; 548/540; 562/844
[58] Field of Search ............... 544/379, 383, 388, 389, 544/390, 60, 121, 366; 514/227.8, 232.2, 235.8, 252, 255

[56] References Cited

U.S. PATENT DOCUMENTS

| | | | |
|---|---|---|---|
| 3,288,795 | 11/1966 | Irikura et al. | 260/288 |
| 4,089,958 | 5/1978 | Freed et al. | 544/389 |
| 4,138,564 | 2/1979 | Freed et al. | 544/346 |
| 4,758,652 | 7/1988 | Hertz et al. | 528/369 |
| 4,923,870 | 5/1990 | Braquest et al. | 514/255 |
| 4,943,578 | 7/1990 | Naylor et al. | 514/252 |
| 5,064,838 | 11/1991 | Carr et al. | 514/317 |

FOREIGN PATENT DOCUMENTS

| | | |
|---|---|---|
| 343900 | 11/1989 | European Pat. Off. |
| 368670 | 5/1990 | European Pat. Off. |
| 436334 | 8/1992 | European Pat. Off. |
| WO90/05525 | 5/1990 | PCT Int'l Appl. |
| WO90/05729 | 5/1990 | PCT Int'l Appl. |
| WO92/01679 | 2/1992 | PCT Int'l Appl. |
| WO92/12128 | 7/1992 | PCT Int'l Appl. |
| WO92/20661 | 11/1992 | PCT Int'l Appl. |

OTHER PUBLICATIONS

Rivett et al *Australian J. Chem.*, 19, 165 (1966).
Korzycka et al., *Pol. J. Pharmacol. Pharm.*, 38, 545 (1986).
Toldy et al., *Acta. Chim. Acad. Sci. Hung.*, 70, 101 (1971).
Bigge et al., *Tetrahedron Lett.*, 30, 5193 (1989).
Soai, et al., *Bull. Chem. Soc. Japan*, 60 (9), 3450–3452 (1987).
Birch, et al., *Bioorg. & Med. Chem. Lett.*, 2 (10), 1275–1278 (1992).
Emonds-Alt, et al., *Life Sci.*, 50, PL-101-PL-106 (1992).
Pat. application Ser. No. 885,416, filed May 19, 1992, by Ashton et al.
Pat. application Ser. No. 905,976, filed Jun. 29, 1992, by Dorn et al.
Pat. application Ser. No. 971,448, filed Nov. 4, 1992, by Dorn et al.
R. S. L. Chang et al., Biochem. and Biophy. Res. Commun., vol. 171, No. 2, pp. 813–817 (Sep. 14, 1990).
S. Whitebread et al., Biochem. and Biophy. Res. Commun., vol. 163, No. 1, pp. 284–291 (Aug. 30, 1989).
Pat. application Ser. No. 935,754, filed Aug. 26, 1992, by Mills et al.

*Primary Examiner*—Emily Bernhardt
*Attorney, Agent, or Firm*—Valerie J. Camara; Mark R. Daniel; Joseph F. DiPrima

[57] ABSTRACT

Diacylpiperazines of general structural formula:

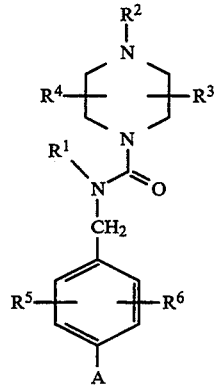

are: angiotensin II (A-II) antagonists with affinity for both $AT_1$ and $AT_2$ receptors useful in the treatment of hypertension, congestive heat failure, cerebrovascular, cognitive, and CNS disorders.

5 Claims, No Drawings

N,N-DIACYLPIPERAZINES

SUMMARY OF THE INVENTION

This invention is concerned with novel compounds represented by structural formula I:

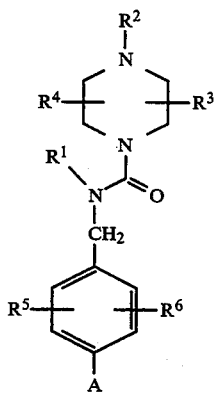

wherein $R^{1-6}$ and A are hereinafter defined.

The invention is also concerned with pharmaceutical formulations with these novel compounds as active ingredients and the use of the novel compounds and their formulations in the treatment of certain (CNS) disorders.

The compounds of this invention have central nervous system (CNS) activity and are useful in the treatment of cognitive dysfunctions including Alzheimer's disease, amnesia and senile dementia. These compounds also have anxiolytic and antidepressant properties and are, therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia.

BACKGROUND OF THE INVENTION

It is now known that there are two subtypes of angiotensin-II (A-II) receptors, the $AT_1$ and $AT_2$ subtypes. Recent studies have shown that in rat brain, A-II receptors are primarily of the $AT_2$ subtype [Chang et al., *Biochem. Biophys. Res. Commun.*, 171, 813 (1990)]. Agents acting as specific antagonists at these brain A-II receptors are of value in the treatment of a variety of cerebrovascular, cognitive and CNS disorders. For example, the utility of compounds having activity at the $AT_2$ receptor is disclosed by Bumpus, et al, *Hypertension*, 17, 720–721 (1991).

Receptors of the $AT_2$ subtype are also found in female reproductive organs of mammals, including uterus (Dudley, et al, *Molecular Pharmacol.*, 38, 370–377 (1990)) and ovaries (Pucell, et al, *Endocrinology*, 128, 1947–1959 (1991)). The role of angiotensin II in processes leading to ovulation has been reviewed (Andrade-Gordon, et al, *Biochem, Pharmacol.*, 42, 715–719 (1991)).

In addition, $AT_2$ receptors are found in neuronal tumor cells (Speth, et al, *Peptide Res.*, 2, 232–239 (1989)) and in transformed human neural cells (Tallant, et al, *Hypertension*, 17, 1135–1143 (1991)).

Some $AT_2$-selective A-II antagonists are known. See for example EP 245,637 and Chang et al., *Mol. Pharmacol*, 29, 347 (1990) which disclose compounds with structures somewhat different from those of the present application and of rather low potency. Also Whitebread et al., *Biochem. Biophys. Res. Commun.*, 163, 284 (1989) describes a peptide with selective $AT_2$ antagonist properties but as with all peptides suffers rapid metabolic breakdown and lack of oral activity. Warner-Lambert PCT Patent Publication No. WO 92/05784 discloses certain $AT_2$-selective A-II antagonists as having a wide variety of utilities.

Some compounds of chemical structures somewhat similar to those of the compounds of the present invention have been reported in U.S. Pat. Nos. 4,089,958 and 4,138,564. However, they are reported as chemical intermediates only.

Some 1,4-bis(diphenylacetyl)piperazines (without substituents on the piperazine ring carbons) have been disclosed as analgesic, antipyretic, and antiinflammatory agents and CNS depressants (U.S. Pat. No. 3,288,795). The preparation of 1,4-bis (diphenylcarbamoyl)piperazine has been reported [D. E. Rivett and J. F. K. Wilshire, *Australian J. Chem.*, 19, 165 (1966)]. Unsymmetrical 1-acyl-4-(diphenylcarbamoyl)piperazines and 1-acyl-4-(dialkylcarbamoyl) piperazines have also been described [L. Korzycka, et al., *Pol. J. Pharmacol. Pharm.*, 38, 545 (1986); L. Toldy, et al., *Acta. Chim. Acad. Sci, Hung.*, 70, 101 (1971)]. All of these are unsubstituted on the piperazine ring carbons.

Certain 1,4-diacylpiperazine-2-carboxylates and related derivatives in which at least one of the acyl groups is substituted benzoyl have been disclosed as platelet-activating factor antagonists (U.S. Pat. No. 4,923,870 and European Patent Application EP 0,368,670). Methyl 4-(benzyloxycarbonyl)-1-(tert-butoxycarbonyl)piperazine-2-carboxylate has been reported as an intermediate (EP 0,368,670), as has methyl 1-(benzyloxycarbonyl)-4-(tert-butoxycarbonyl)piperazine-2-carboxylate and the coresponding acid [C. F. Bigge, et al., *Tetrahedron Lett.*, 30, 5193 (1989).

DETAILED DESCRIPTION OF THE INVENTION

The novel compounds of this invention are represented by structural formula I:

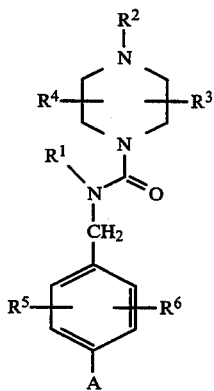

or a pharmaceutically acceptable salt thereof, wherein:
A is selected from:

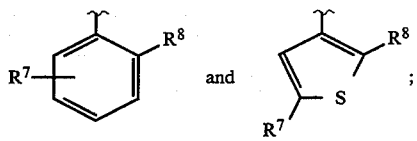

R¹ is selected from the group consisting of:
1) H,
2) $C_{1-8}$ alkyl,
3) $C_{3-7}$ cycloalkyl,
4) phenyl, either unsubstituted or substituted with one or two substituents selected from:
 a) —$C_{1-4}$ alkyl,
 b) —halo,
 c) —OH,
 d) —$CF_3$,
 e) —$NH_2$,
 f) —$NH(C_{1-4}$ alkyl),
 g) —$N(C_{1-4}$ alkyl$)_2$,
 h) —$CO_2H$,
 i) —$CO_2(C_{1-4}$ alkyl), and
 j) —$C_{1-4}$ alkoxy; or
5) $C_{1-4}$ alkyl-aryl, wherein the aryl is phenyl or naphthyl, either unsubstituted or substituted with one or two substitutents selected from:
 a) —$C_{1-4}$ alkyl,
 b) —halo,
 c) —OH,
 d) —$CF_3$
 e) —$NH_2$,
 f) —$NH(C_{1-4}$ alkyl),
 g) —$N(C_{1-4}$ alkyl$)_2$,
 h) —$CO_2H$,
 i) —$CO_2(C_{1-4}$ alkyl), and
 j) —$C_{1-4}$ alkoxy;

R² is selected from the group consisting of:
1) —$C_{1-6}$ alkyl,
2) —$CH_2$aryl,
3) —$CH_2$—$C_{3-7}$ cycloalkyl,
4) —$CO_2R^{2a}$,
5) —$CON(R^{2a}R^{2b})$,
6) —$SO_2N(R^{2a}R^{2b})$,
7) aryl,
8) —CO-aryl, and
9) —CO—$C_{1-4}$ alkyl;

$R^{2a}$ and $R^{2b}$ are independently selected from the group consisting of:
1) hydrogen,
2) —$C_{1-8}$ alkyl,
3) —$C_{1-8}$ alkyl-$NH(C_{1-8}$ alkyl),
4) —$C_{1-8}$ alkyl-$NH(C_{1-8}$ alkyl$)_2$,
5) -aryl,
6) —$CH_2$-aryl,
or wherein —$NR^{2a}R^{2b}$ may form a heterocyclic ring of the form —$N(CH_2CH_2)_2L$, wherein L is selected from the group consisting of O, S, N—$C_{1-4}$alkyl, N-aryl, and N—CO—$C_{1-4}$ alkyl;

R³ is selected from the group consisting of:
1) —$CO_2R^{2a}$,
2) —$CON(R^{2a}R^{2b})$,
3) —$CH_2S$—$C_{1-4}$alkyl, and
4) —$CH_2O$—$C_{1-4}$alkyl;

R⁴ is independently selected from:
1) H,
2) —$C_{1-6}$alkyl, and
3) —R³;

R⁵ is selected from the group consisting of:
1) hydrogen,
2) —$C_{1-6}$alkyl
3) —$C_{2-6}$alkenyl,
4) —$C_{2-4}$alkynyl,
5) halo,
6) —O—$C_{1-4}$alkyl,
7) —$CF_3$,
8) —CN, and
9) —$CH_2O$—$C_{1-4}$alkyl, R⁶ is independently selected from
1) H, and
2) R⁵;

R⁷ is selected from the group consisting of:
1) —$C_{1-6}$alkyl
2) —$C_{2-6}$alkenyl,
3) —$C_{2-4}$alkynyl,
4) halo,
5) aryl,
6) —$CH_2$-aryl,
7) —O—$C_{1-4}$alkyl,
8) —$CF_3$,
9) —CN, and
10) —$CH_2O$—$C_{1-4}$alkyl;

R⁸ is selected from the group consisting of:
1) —$CO_2R^9$, wherein $R^9$ is hydrogen or $C_{1-6}$alkyl,
2) 1H-tetrazol-5-yl,
3) —$CONHSO_2R^{10}$, wherein $R^{10}$ is selected from:
 a) —$C_{1-6}$ alkyl,
 b) —$C_{1-6}$ alkoxy,
 c) aryl,
 d) —$CH_2$aryl, and
 e) —$CH(aryl)_2$,
4) —$SO_2NHR^{10}$,
5) —$NHSO_2R^{10}$,
6) —$SO_2NHCOR^{10}$,
7) —$NHSO_2CF_3$, and
8) —$SO_2NHCO_2R^{10}$.

The term "aryl" means phenyl or naphthyl either unsubstituted or substituted with one, two or three substituents selected from the group consisting of halo, $C_{1-4}$-alkyl, $C_{1-4}$-alkoxy, $NO_2$, $CF_3$, $C_{1-4}$-alkylthio, OH, —$N(R^{2a}R^{2b}$, —$CO_2R^{2a}$, $C_{1-4}$-perfluoroalkyl, $C_{3-6}$-perfluorocycloalkyl, and tetrazol-5-yl.

The term "heteroaryl" means an unsubstituted, monosubstituted or disubstituted five or six membered aromatic heterocycle comprising from 1 to 3 heteroatoms selected from the group consisting of O, N and S and wherein the substituents are members selected from the group consisting of —OH, —SH, —$C_{1-4}$-alkyl, —$C_{1-4}$-alkoxy, —$CF_3$, halo, —$NO_2$, —$CO_2R^{2a}$, —$N(R^{2a}R^{2b})$ and a fused benzo group;

The term "halo" means —Cl, —Br, —I or —F.

The term "alkyl", "alkenyl", "alkynyl" and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

One embodiment of the novel compounds of this invention is that structural formula:

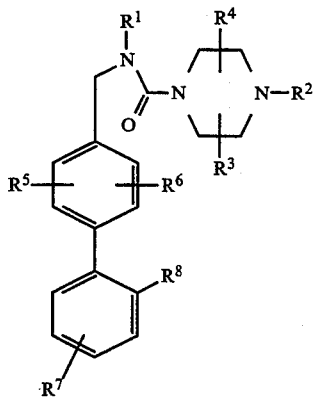

or a pharmaceutically acceptable salt thereof.

Specific compounds within the present invention include:

1) (S)-1-(Diphenylcarbamoyl)-4-N-pentyl-N-[2-(1H-tetrazol-5-yl]biphenyl-4-yl)-methyl]carbamoyl]-piperazine-2-carboxylic acid;
2) (S)-4-(Dipentylcarbamoyl)-1-[N-pentyl-N-[2-(1H-tetrazol-5-yl)biphenyl-4-yl)methyl]carbamoyl]-piperazine-2-carboxylic acid;
3) (S)-4-(Diphenylcarbamoyl)-1-{N-pentyl-N-[2-(1H-tetrazol-5-yl)biphenyl-4-yl)methyl]carbamoyl}-piperazine-2-carboxylic acid;
4) (S)-1-(Diphenylcarbamoyl)-4-{N-pentyl-N-[2-(1H-tetrazol-5-yl]-5-(propyl)-biphenyl-4-yl)-methyl]-carbamoyl}-piperazine-2-carboxylic acid;
5) (S)-1-(Diphenylcarbamoyl)-4-{N-pentyl-N-[2-(1H-tetrazol-5-yl]-5-propyl-3-thienyl)phenyl]-methyl]-carbamoyl}-piperazine-2-carboxylic acid; and
6) (S)-4-(Dipentylcarbamoyl)-1-(diphenylcarbamoyl)-piperazine-2-(3-morpholinopropyl)carboxamide.

The useful central nervous system (CNS) activities of the compounds of this invention are demonstrated and exemplified by the following assays.

COGNITIVE DYSFUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced stereotypy model. A clinically useful antipsychotic drug that is used as a positive control in this assay is haloperidol. The assay method is based upon the observation that stimulation of the dopaminergic system in rats produces stereo-typed motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer.

Compounds of the invention should be efficacious in this assay in the range of from about 0.1 mg/kg to about 100 mg/kg.

Angiotensin II (AII) is a powerful arterial vasoconstrictor, and it exerts its action by interacting with specific receptors present on cell membranes. In order to identify AII antagonists and determine their efficacy in vitro, the following two ligand-receptor binding assays were established.

Receptor binding assay using rabbit aortae membrane preparation:

Three frozen rabbit aortae (obtained from Pel-Freeze Biologicals) are suspended in 5 mM Tris-0.25M Sucrose, pH 7.4 buffer (50 ml) homogenized, and then centrifuged. The mixture is filtered through a cheesecloth and the supernatant is centrifuged for 30 minutes at 20,000 rpm at 4° C. The pellet thus obtained is resuspended in 30 ml of 50 mM Tris-5 mM $MgCl_2$ buffer containing 0.2% Bovine Serum Albumin and 0.2 mg/ml Bacitration and the suspension is used for 100 assay tubes. Samples tested for screening are done in duplicate. To the membrane preparation (0.25 ml) there is added $^{125}$I-Sar$^1$Ile$^8$-angiotensin II [obtained from New England Nuclear] (10 ul; 20,000 cpm) with or without the test sample and the mixture is incubated at 37° C. for 90 minutes. The mixture is then diluted with ice-cold 50 mM Tris-0.9% NaCl, pH 7.4 (4 ml) and filtered through a glass fiber filter (GF/B Whatman 2.4″ diameter). The filter is soaked in scintillation cocktail (10 ml) and counted for radioactivity using Packard 2660 Tricarb liquid scintillation counter. The inhibitory concentration ($IC_{50}$) of a potential AII antagonist which gives 50% displacement of the total specifically bound $^{125}$I-Sar$^1$Ile$^8$-angiotensin II is presented as a measure of the efficacy of such compounds as AII antagonists.

Receptor assay using Bovine adrenal cortex preparation

Bovine adrenal cortex is selected as the source of AII receptor. Weighed tissue (0.1 g is needed for 100 assay tubes) is suspended in Tris.HCl (50 mM), pH 7.7 buffer and homogenized. The homogenate is centrifuged at 20,000 rpm for 15 minutes. Supernatant is discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there is added 3H-angiotensin II (50 mM) (10 ul) with or without the test sample and the mixture is incubated at 37° C. for 1 hour. The mixture is then diluted with Tris buffer (4 ml) and filtered through a glass fiber filter (GF/B Whatman 2.4″ diameter). The filter is soaked in scintillation cocktail (10 ml) and counted for radioactivity using Packard 2660 Tricarb liquid scintillation counter. The inhibitory concentration ($IC_{50}$) of a potential AII antagonist which gives 50% displacement of the total specifically bound $^3$H-angiotensin II is presented as a measure of the efficacy of such compounds as AII antagonists.

Receptor assay using rat brain membrane preparation

Membranes from rat brain (thalamus, hypothalamus and midbrain) are prepared by homogenization in 50 mM Tris HCl (pH 7.4), and centrifuged at 50,000×g. The resulting pellets are washed twice in 100 mM NaCl, 5 mM $Na_2$.EDTA, 10 mM $Na_2HPO_4$ (pH 7.4) and 0.1 mM PMSF by resuspension and centrifugation. For binding assays, the pellets are resuspended in 160 volumes of binding assay buffer (100 mM NaCl, 10 mM $Na_2HPO_4$, 5 mM $Na_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$,Ile$^8$-angiotensin II (1 μM) (for nonspecific binding) or test compounds (for displacement) and 10 μl of [$^{125}$I]Sar$^1$-,Ile$^8$-angiotensin II (23–46 pM) are added to duplicate tubes. The receptor membrane preparation (500 μl) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters is counted using a gamma counter.

Using the methodology described above, representative compounds of this invention could be evaluated and an $IC_{50}<50$ μM determined, thereby demonstrating and confirming the utility of the compounds of the invention as effective A II antagonists.

The antihypertensive effects of the compounds described in the present invention may be evaluated using the methodology described below:

Male Charles River Sprague-Dawley rats (300–375 gm) are anesthetized with methohexital (Brevital; 50 mg/kg i.p.) and the trachea is cannulated with PE 205 tubing. A stainless steel pithing rod (1.5 mm thick, 150 mm long) is inserted into the orbit of the right eye and down th spinal column. The rats are immediately placed on a Harvard Rodent Ventilator (rate—60 strokes per minute, volumn—1.1 cc per 100 grams body weight). The right carotid artery is ligated, both left and right vagal nerves are cut, and the left carotid artery is cannulated with PE 50 tubing for drug administration, and body temperature is maintained at 37° C. by a thermostatically controlled heating pad which received input from a rectal temperature probe. Atropine (1 mg/kg i.v.) is then administered, and 15 minutes later propranolol (1 mg/kg i.v.). Thirty minutes later antagonists of formula I are administered intravenously or orally. Angiotensin II is then typically given at 5, 10, 15, 30, 45 and 60 minute intervals and every half-hour thereafter for as long as the test compound showed activity. The change in the mean arterial blood pressure is recorded for each angiotensin II challenge and the precent inhibition of the angiotensin II response is calculated.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

The compounds of the present invention antagonize the binding of angiotensin II to $AT_2$ receptors and are useful in treating disorders of the CNS which are attributed to the binding of angiontension II to $AT_2$ receptors. The compounds of the present invention are additionally useful in treating conditions of the female reproductive system which result from the binding of angiotensin II to $AT_2$ receptors in reproductive organs. The compounds of the present invention are also useful as anticancer agents for brain cancers and other cancers wherein the $AT_2$ receptor is prevelant.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam and buspirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

Typically, the individual daily dosages for these combinations can range from about one-fifth of the minimally recommended clinical dosages to the maximum recommended levels for the entities when they are given singly.

To illustrate these combinations, an angiotensin II antagonist of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

Several methods for preparing the compounds of this invention are illustrated in the following Schemes and Examples.

ABBREVIATIONS USED IN SCHEMES AND EXAMPLES

TABLE 1

| Reagents: | |
|---|---|
| Et$_3$N | triethylamine |
| Ph$_3$P | triphenylphosphine |
| TFA | trifluoroacetic acid |
| NaOEt | sodium ethoxide |
| DCC | N,N'-dicyclohexylcarbodiimide |
| DCU | N,N'-dicyclohexylurea |
| CDI | 1,1'-carbonyldiimidazole |
| MCPBA | m-chloroperbenzoic acid |
| DBU | 1,8-diazabicyclo[5.4.0]undec-7-ene |
| Cbz-Cl | benzyl chloroformate |
| iPr$_2$NEt or DIEA | N,N-diisopropylethylamine |
| NHS | N-hydroxysuccinimide |
| DIBAL | diisobutylaluminum hydride |
| Me$_2$SO$_4$ | dimethyl sulfate |
| HOBt | 1-hydroxybenzotriazole hydrate |
| EDAC | 1-ethyl-3-(3-dimethylaminopropyl)carbodiimide hyrochloride |
| Solvents: | |
| DMF | dimethylformamide |
| THF | tetrahydrofuran |
| MeOH | methanol |
| EtOH | ethanol |
| AmOH | n-amyl alcohol |
| AcOH | acetic acid |
| MeCN | acetonitrile |
| DMSO | dimethylsulfoxide |
| Others: | |
| Ph | phenyl |
| Ar | aryl |
| Me | methyl |
| Et | ethyl |
| iPr | isopropyl |
| Am | n-amyl |
| Cbz | carbobenzyloxy (benzyloxycarbonyl) |
| Boc | tert-butoxycarbonyl |
| PTC | phase transfer catalyst |
| cat. | catalytic |
| FAB-MS | fast atom bombardment mass spectrometry |

For the synthesis of compounds of formula I, the central piperazine nucleus may be constructed by various methods. One such useful method, shown in Scheme 1, entails catalytic hydrogenation of a substituted pyrazine 1 to give the piperazine 2 [E. Felder, et al., Helv. Chim. Acta, 43, 888 (1960)]. This is typically accomplished by use of palladium on carbon as the catalyst, in a solvent such as ethanol or water, at a temperature of 20°–50° C.

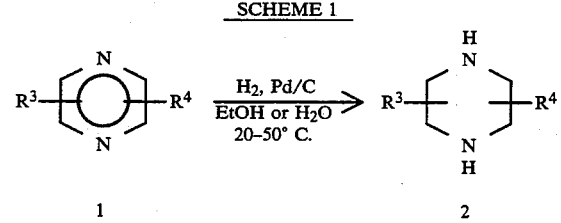

SCHEME 1

Another method (Scheme 2) involves reaction of a protected diamine 3 with a dibromo compound 4 in the presence of base at elevated temperature to give the bis-protected piperazine 5, which yields 2 upon deprotection. This method has been particularly useful in cases where 4 is a 2,3-dibromo ester. In the variation used by Piper, et al. [J. R. Piper, L. M. Rose, and T. P. Johnston, J. Org. Chem., 37, 4476 (1972)], the protecting group P is p-toluenesulfonyl, and the disodium salt of 3 is heated with 4 (R=CO$_2$Et) in DMF at up to about 100°–110° C. to form the piperazine 5. The p-toluenesulfonyl protecting groups can be removed (along with simultaneous ester hydrolysis) by heating 5 at reflux in 48% HBr [F. L. Bach, Jr., et al., J. Am. Chem. Soc., 77, 6049 (1955). In another variation [E. Jucker and E. Rissi, Helv. Chin. Acta, 45, 2383 (1962)], the protecting group P is benzyl, and heating 3 with 4 (R$^4$=CO$_2$Et) in benzene yields 5. In this case deprotection is achieved (without ester hydrolysis) by palladium-catalyzed hydrogenation in acetic acid.

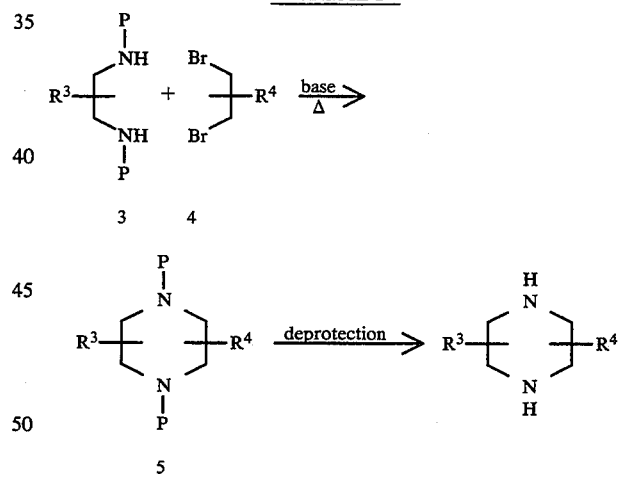

SCHEME 2 where P is a protecting group

Another route to piperazine-2-carboxylic acids is illustrated in Scheme 3. The α-Cbz-protected α,β-diamino ester 6 is reacted with α-bromo ester 7. Following hydrogenolyis of the Cbz group, the ox-opiperazinecarboxylate 8 is obtained. Selective reduction and hydrolysis affords the piperazinecarboxylic acid 9. This route [B. Aebischer, et al., Helv. Chim. Acta, 72, 1043 (1989)] has been used (for R$^3$=H) to prepare chiral piperazine-2carboxylic acid from a chiral diamino ester 6. Optically active piperazine-2-carboxylic acids have also been obtained from the racemate via a camphorsulfonic acid salt [E. Felder, Helv. Chim. Acta, 43, 888 (1960)] or menthyl ester [B. Aebischer, et Helv. Chim. Acta, 72, 1043 (1989)].

SCHEME 3

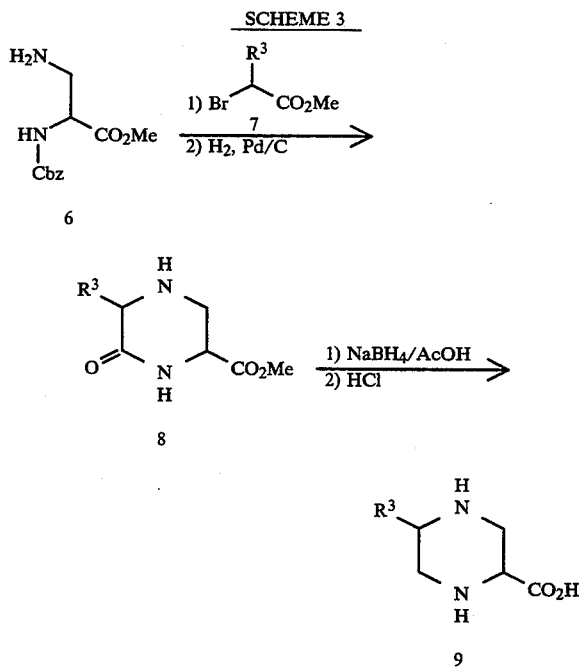

For the subclass of compounds of formula I the acylation (or carbamoylation) of the piperazine nucleus may be accomplished straightforwardly in a single step. An example is shown in Scheme 4. Thus piperazine-2-carboxylic acid dihydrohalide (10) [F. L. Bach, Jr., et al., *J. Am. Chem. Soc.*, 77, 6049 (1955); E. Felder, et al., *Helv. Chim. Acta*, 43, 888 (1960)] in the presence of excess aqueous sodium hydroxide and a cosolvent such as acetonitrile may be treated with two equivalents of a carbamoyl chloride 11, preferably at about 0°–5° C. to afford the product 12. A similar reaction can be carried out with an acid chloride analogous to 11 in which N is replaced by CH.

SCHEME 4

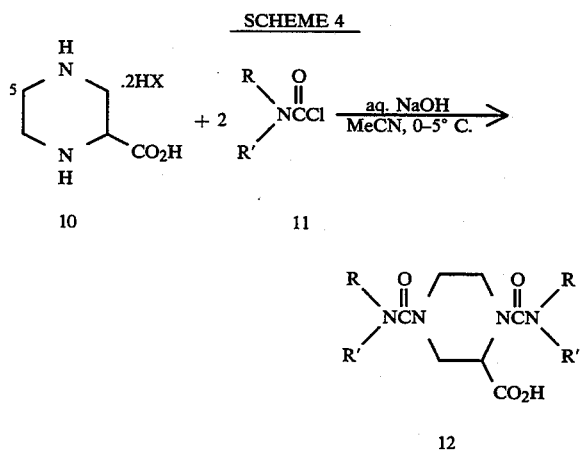

where $R = R^{1a} = R^{2a}$, $R' = R^{1b} = R^{2b}$ and $X = Cl, Br$, etc.

The acylations (or carbamoylations, etc.) may also be performed in stepwise fashion. In the case of piperazine-2-carboxylic acid, a very useful method is to prepare a copper(II) complex, which blocks $N^1$ and allows the regiospecific synthesis of the $N^4$—Cbz derivative. After removal of copper(II), $N^1$ may then be acylated or carbamoylated. Upon deprotection to remove the Cbz group, $N^4$ is then available for introduction of a new acyl or carbamoyl group.

Such a pathway is illustrated in Scheme 5. By the method of M. E. Freed and J. R. Potoski [U.S. Pat. No. 4,032,639 (1977)], 10 is treated with basic cupric carbonate to generate the copper(II) complex, then reacted with Cbz-chloride in the presence of aqueous sodium bicarbonate and acetone, and finally treated with $H_2S$ gas in the presence of aqueous HCl to break down the copper(II) complex, liberating 4-(benzyloxy-carbonyl)-2-piperazinecarboxylic acid (13). Variations include the use of cupric chloride at pH 9.5 to form the copper(II) complex and the use of Dowex 50 ($H^+$ form) to ultimately remove the copper(II) ion. Treatment of 13 with acylating agent 14 in the presence of base (for example, aqueous sodium hydroxide in acetone or a tertiary amine in DMF or THF) gives 15. The Cbz group of 15 is removed by hydrogenation using palladium on carbon as catalyst in a solvent such as acetic acid, yielding 16. An alternative method of Cbz removal, the use of anhydrous HBr in acetic acid, is preferred when $R^{1a}$ and/or $R^{1b}$ in 15 contain functional groups unstable to hydrogenation. Next, 16 is treated with reagent 17 which may be, for example, a carbamoyl chloride, a carboxylic acid N-hydroxysuccinimide ester, an acyl imidazolide, or a carboxylic acid chloride. This reaction is preferably conducted in the presence of a tertiary amine base such as triethylamine or N,N-diisopropylethylamine in a solvent such as THF or DMF. The reaction is typically conducted at about 20°–50° C. or, in the case of a carboxylic acid chloride, at about 0° C., to give the product 18.

SCHEME 5

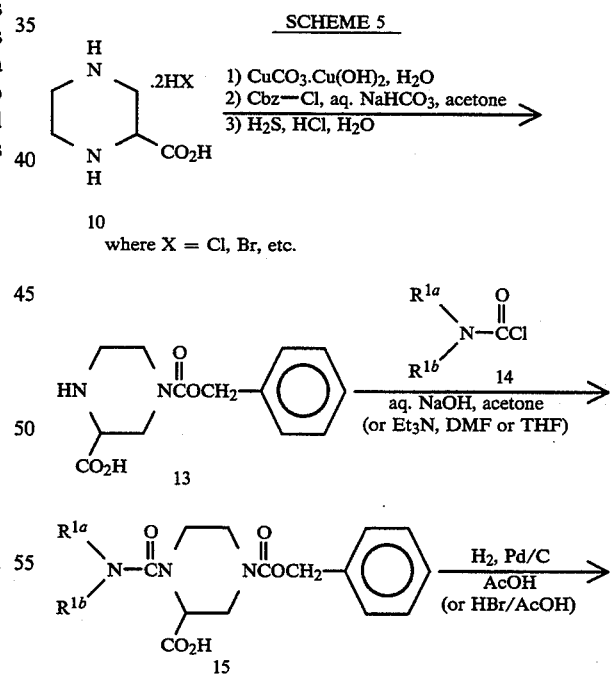

where X = Cl, Br, etc.

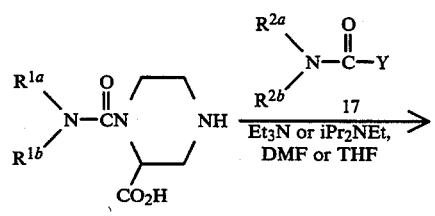

SCHEME 5 (continued)

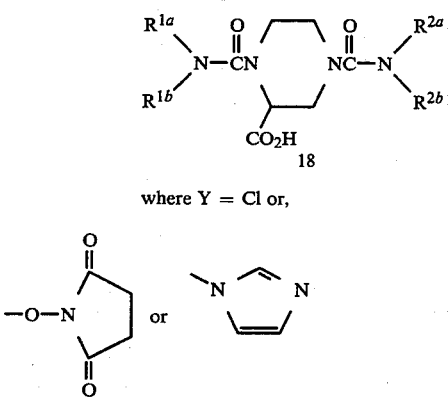

where Y = Cl or,

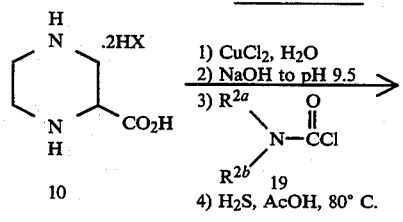

It is sometimes advantageous to avoid the intermediacy of Cbz protection in the synthesis of compounds of structure 18. In Scheme 6, a salt of piperazine-2-carboxylic acid (10) is converted in situ to the copper(II) complex and then treated directly with acylating agent 19 (equivalent to 17 where Y=Cl) in acetone in the presence of aqueous sodium hydroxide. Subsequent treatment with $H_2S$ in acetic acid at about 80° C. liberates 20. Reaction of 20 with acylating agent 14 (for example, in DMF in the presence of a base such as N,N-diisopropylethylamine) affords 18.

SCHEME 6

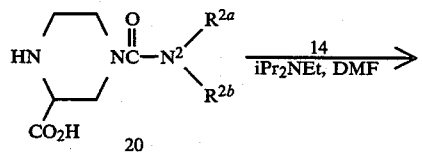

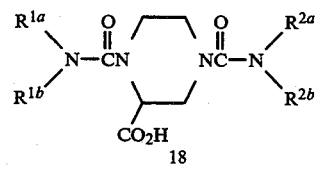

Mono-N-protected piperazine-2-carboxylate esters are also useful intermediates for the synthesis of compounds of formula I. Thus, intermediates 21 [H. Sugihara and K. Nishikawa, European Patent Application EP 368,670 (1990)], 22 (Sugihara and Nishikawa, op. cit.), 23 (Sugihara and Nishikawa, op. cit.), and 24 [C. F. Bigge, et al., *Tetrahedron Lett.*, 30, 5193 (1989)] may all be subjected to an acylation-deprotection-acylation sequence to give 25, as shown in Scheme 7. Acylation (or carbamoylation, etc.) conditions are as described above. The Cbz group is generally removed by catalytic hydrogenation, as discussed above, whereas the Boc group is generally removed either with anhydrous trifluoroacetic acid (neat or in methylene chloride) or with anhydrous HCl in a solvent such as ethyl acetate.

SCHEME 7

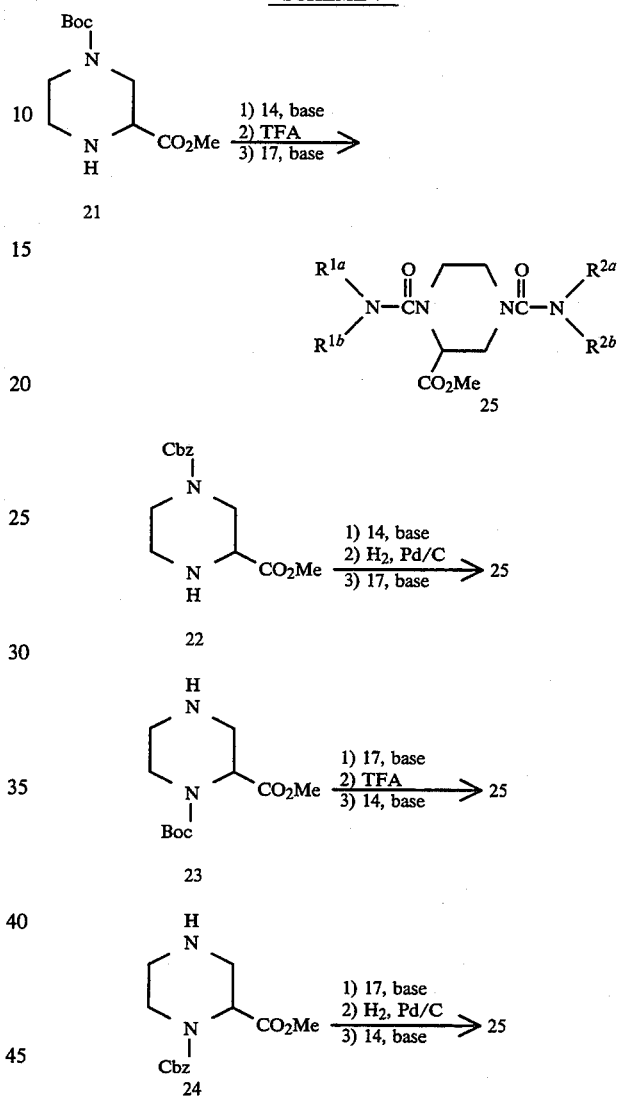

Reagents such as 14, 17, or 19 for acylation (or carbamoylation or oxycarbonylation) of the piperazine are prepared by methods well known in the literature. Several of these standard methods are shown in Scheme 8. For example, a secondary amine 26 is reacted with phosgene to give the carbamoyl chloride 27. The reaction may be carried out either by heating a solution of the amine and phosgene in toluene at about 90° C. or by conducting the reaction in a two-phase system of toluene and aqueous sodium hydroxide at about −5° C. In the case of primary amine 28 (equivalent to 26 where $R^b$=H), heating with phosgene in toluene yields the isocyanate 29, which can be reacted with a piperazine derivative in the same fashion as a carbamoyl chloride. One route to an N-aryl-N-alkyl(or aralkyl) carbamoyl chloride 33 is via reductive alkylation. Thus arylamine 30 and aldehyde 31 are reacted in the presence of sodium borohydride in a solvent such as ethanol to give the secondary amine 32, which is converted to 33 with phosgene as described above.

The N,N-diarylcarbamoyl chloride 33e is similarly obtained from the diarylamine 33d, which may be obtained via an Ullmann-type coupling. In one variant [cited in D. Schmidling and F. E. Condon, *Baskerville Chem. J. City Coll, N.Y.*, 12, 22 (1963)], the acetanilide derivative 33a is reacted with aryl bromide 33b in the presence of copper and potassium carbonate neat or in nitrobenzene at reflux to give the N,N-diaryl amide 33c, which is then hydrolyzed to 33d (for example, by heating with 70% sulfuric acid or with ethanolic KOH) [H. S. Freeman, J. R. Butler and L. D. Freedman, *J. Org. Chem.*, 43, 4975 (1978)]. In another variant [D. Schmidling and F. E. Condon, op. cit.; S. Kurzepa and J. Cieslak, *Roczniki Chem.*, 34, 111 (1960)], arylamine 30 is coupled with the orthobromobenzoic acid derivative 33f by heating at reflux in amyl alcohol in the presence of potassium carbonate and copper. The resulting product 33g, upon heating to about 220°–260° C., undergoes decarboxylation to 33d.

Chloroformate 35 is readily prepared from alcohol 34 with phosgene in toluene, typically at 0°–20° C. Carboxylic acid 36 may be converted to the acid chloride 37 by treatment with thionyl chloride (for example in benzene at 80° C). Treatment of 36 with N-hydroxysuccinimide (NHS) in the presence of N,N'-dicyclohexylcarbodiimide (DCC) in a solvent such as acetonitrile provides the reactive N-hydroxysuccinimide ester. The acylimidazolide 39, also a useful acylating agent which may be prepared in situ, is obtained by treatment of 36 with 1,1'-carbonyldiimidazole (CDI) in a solvent such as THF.

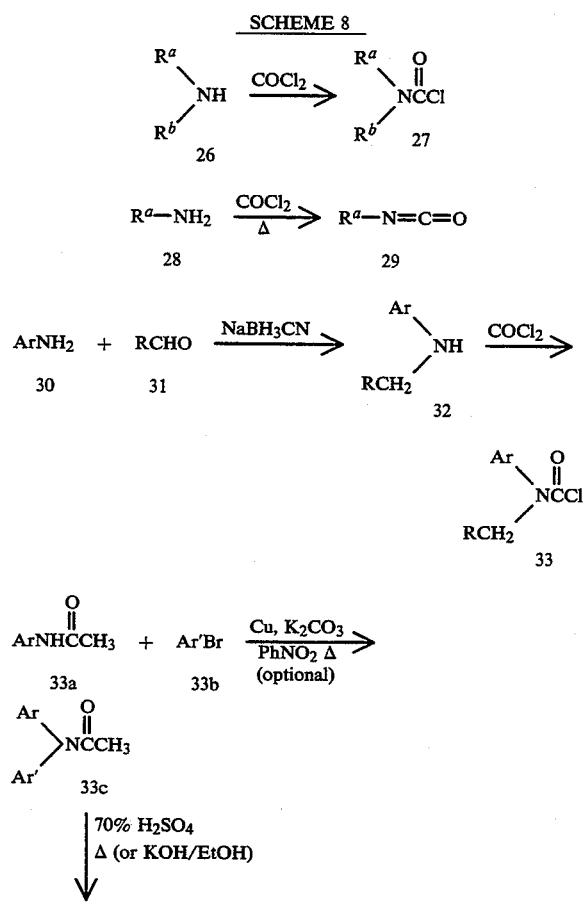

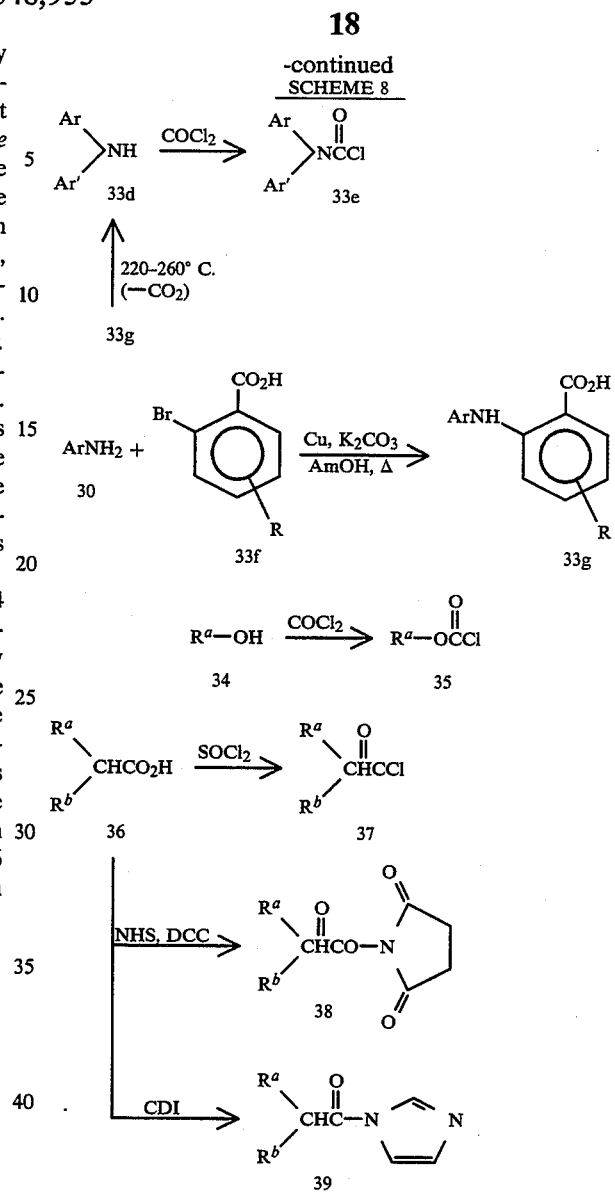

In compounds of formula 1, the $R^3$ and $R^4$ substituents may be present at the time the piperazine ring system is formed, as shown in Schemes 1–3. However, additional transformations may be carried out on the $R^3$ and/or $R^4$ functional groups after elaboration of the diacylated (or carbamoylated, etc.) piperazine, as shown in Scheme 9. For example, piperazinecarboxylic acid 40 may be readily converted to its methyl ester 41 by treatment with diazomethane, preferably in ether-methanol or THF at 0°–25° C. [B. Aebischer, et al., *Helv. Chim. Acta*, 72, 1043 (1989); C. F. Bigge, et al., *Tetrahedron Lett.*, 30, 5193 (1990)] or by other methods (C. F. Bigge, et al., op. cit.). The acid 40 may also be obtained by saponification of 41 under standard conditions. The methyl ester 41 may also be reduced to alcohol 42 by treatment with sodium borohydride/methanol according to the procedures of Sugihara and Nishikawa (EP 0,368,670). Treatment of carboxylic acid 40 with DCC or EDAC/HOBt followed by amine 43 affords the amide 44. Methyl ester 41 may be transformed to aldehyde 45 by use of diisobutylaluminum hydride under controlled conditions at −78° C. Alternatively, alcohol 42 can be oxidized to 45 by various methods, such as the use or catalytic tetrapropylammonium perruthenate (TPAP) and 4-methylmorpholine N-oxide (NMO) in the presence of molecular sieves [W. P. Griffith, et al., *J. Chem. Soc. Chem. Commun.*, 1625 (1987)]. Using standard reductive alkylation conditions, 45 is reacted with amine 43 in the presence of sodium cyanoborohydride to give the aminomethylpiperazine 46. Alcohol 42 may be converted to methyl ether 47 by use of dimethyl sulfate, 50% aqueous sodium hydroxide, and a phase transfer catalyst (PTC) such as tetrabutylammonium hydrogen sulfate [A. Merz, *Angew. Chem. Int. Ed. Engl.*, 12, 846 (1973).

The acylsulfonamide derivative 48 is obtained by treating the carboxylic acid 40 with carbonyldiimidazole and then with the sulfonamide, $RSO_2NH_2$, and DBU as base in a solvent such as THF. Treatment of alcohol 42 with the carbamoyl chloride 49 in the presence of a base such as N,N-diisopropylethylamine yields the carbamate 50. Similarly, reaction of 42 with acid chloride 51 in the presence of a base like pyridine gives the acyloxymethylpiperazine 52. The bromomethyl intermediate 53 is available by treatment of alcohol 42 with triphenylphosphine and carbon tetrabromide. Displacement of the bromo group by a thiol 54 occurs in the presence of N,N-diisopropylethylamine as base to give the thioether 55. Oxidation of 55 to the sulfoxide 56 or the sulfone 57 may be carried out with m-chloroperbenzoic acid (MCPBA) in a solvent such as methylene chloride or acetic acid. Whether 56 or 57 is the major or exclusive product is dependent on the stoichiometry, reaction time, and temperature.

Besides the methyl ester 41, the carboxylic acid 40 may be converted into other esters 58, for example by treatment with carbonyldiimidazole and an alcohol, ROH, in the presence of catalytic sodium ethoxide [H. A. Staab and A. Mannschreck, *Chem. Ber.*, 95, 1284 (1962)]. An α-(acyloxy)alkyl ester 60 may be obtained by reaction of 40 with an α-chloralkyl ester 59 in the presence of triethylamine, sodium iodide, and tetrabutylammonium hydrogen sulfate as phase transfer catalyst [E. W. Petrillo, et al., U.S. Pat. No. 4,873,356 (1989)].

SCHEME 9

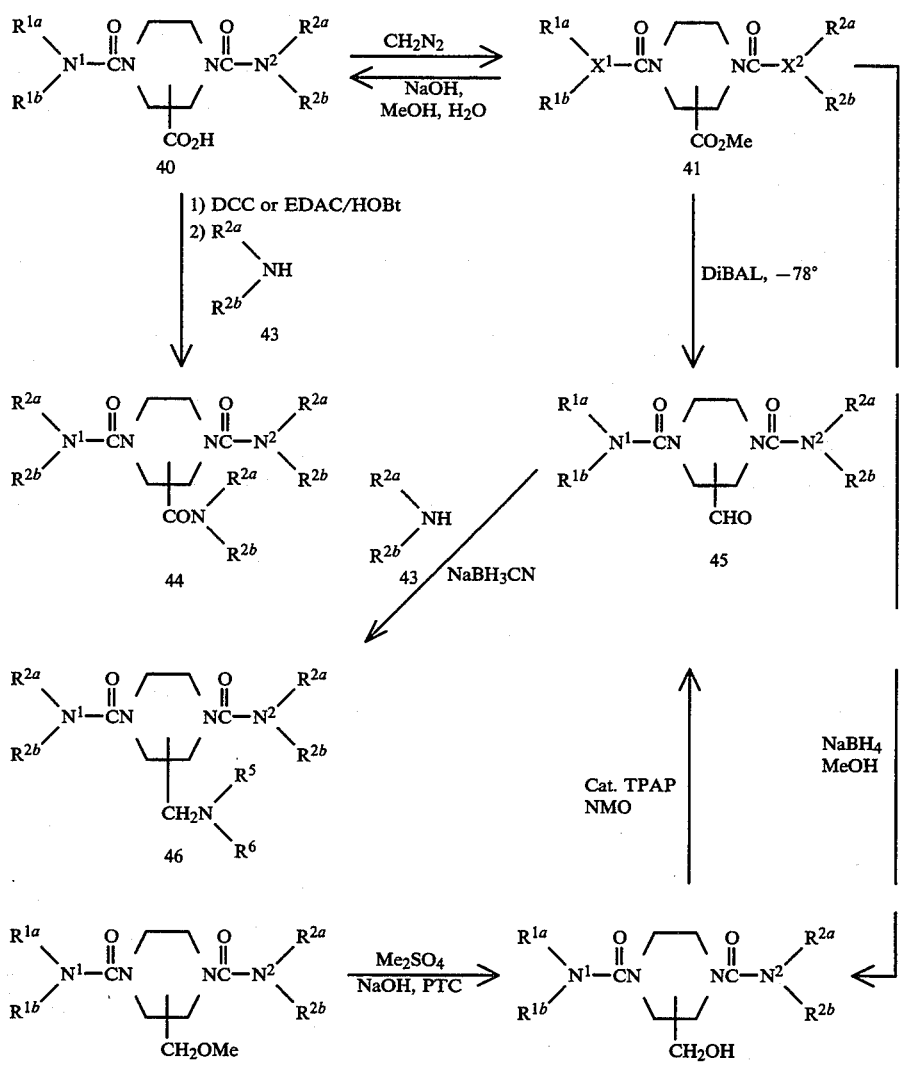

SCHEME 9
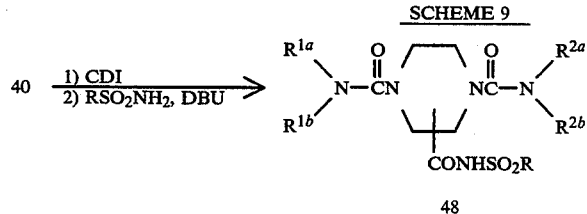
48
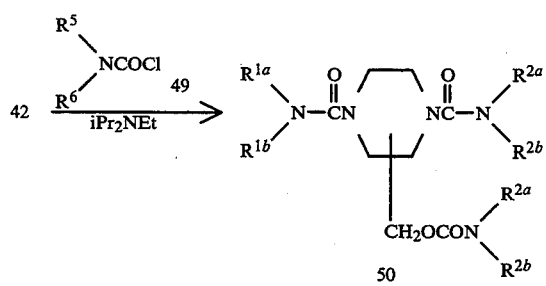
50
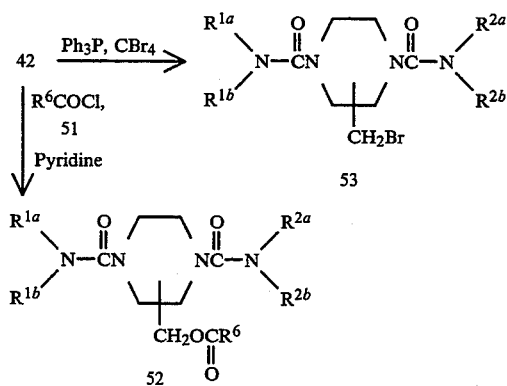
52, 53
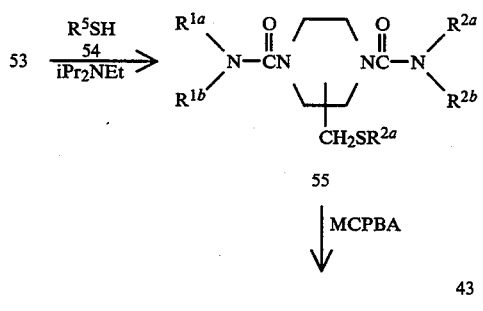
55
↓ MCPBA
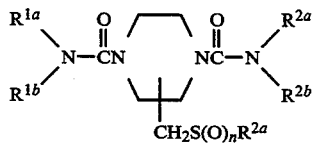
56, n = 1
57, n = 2
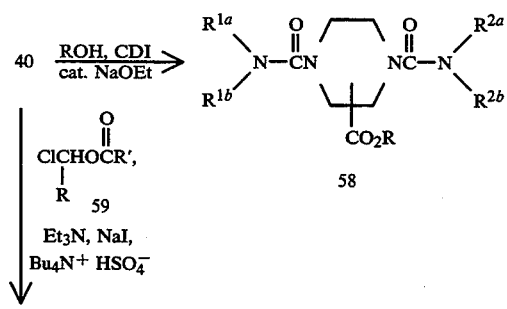
58

SCHEME 9

-continued

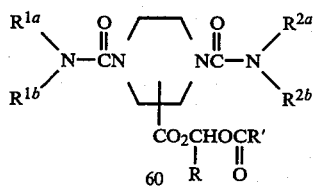

Thiophene-substituted compounds may be prepared by modification of the procedures disclosed in U.S. Pat. No. No. 5,177,074.

The object compounds of Formula I obtained according to the reactions as explained above can be isolated and purified in a conventional manner, for example, extraction, precipitation, fractional crystallization, recrystallization, chromatography, and the like.

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, pictate, pivalate, propionate, succinate, tartrate, tosylate, and undecanoate. Base salts include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Although the reaction schemes described herein are reasonably general, it will be understood by those skilled in the art of organic synthesis that one or more functional groups present in a given compound of formula I may render the molecule incompatible with a particular synthetic sequence. In such a case an alternative route, an altered order of steps, or a strategy of protection and deprotection may be employed. In all cases the particular reaction conditions, including reagents, solvent, temperature, and time, should be chosen so that they are consistent with the nature of the functionality present in the molecule.

EXAMPLE 1

(±)-4-(Benzyloxycarbonyl)-1-(diphenylacetyl)-2-piperazinecarboxylic acid

A solution of 2.64 g (10 mmole) of (±)-4-benzyloxycarbonyl)-2-piperazinecarboxylic acid [M. E. Freed and J. R. Potoski, U.S. Pat. No. 4,032,639 (1977)] in 11.2 ml (11.2 mmole) of 1N NaOH was diluted with 11.2 ml of acetone. This solution was stirred vigorously at room temperature as a solution of 2.31 g (10 mmole) of diphenylacetyl chloride in 10 ml of acetone was added dropwise in portions, alternating with dropwise addition of small portions of 2.5N NaOH [as necessary to maintain basic pH; total addition, 4 ml (10 mmole)]. After the addition was complete and the pH was no longer changing, the solution was stirred for approximately 1 hour and then filtered to remove a small amount of insoluble material. The filtrate was diluted with 30 ml of $H_2O$ and shaken with 50 ml of ether. The aqueous layer was separated and acidified with 2.5N HCl just to the point of full separation of a second oily phase. The oil was extracted with a mixture of 40 ml of ether and 10 ml of $CH_2Cl_2$. The organic phase was dried over $MgSO_4$, treated with charcoal, and filtered through Celite. Concentration of the filtrate in vacuo gave a yellow-orange oil, which partially crystallized on standing. Trituration with a few ml of ether resulted in gradual crystallization of the remainder. Finally, the crystalline mass was collected on a filter, ground to a powder, and washed with small volumes of ether to yield, after drying, 3.19 g (70%) of cream-colored powder, mp 183.5°–185.5° C.; homogeneous by TLC in 90:10:1 $CHCl_3$—MeOH—$H_2$. The $^1H$ NMR indicated a mixture of rotameric forms.

Mass spectrum (FAB): m/e 459 (M+1). Analysis ($C_{27}H_{26}N_2O_5.0.25\ H_2O$): Calculated: C, 70.04; H, 5.77; N, 6.05 Found: C, 70.03; H, 5.63; N, 5.95 $^1H$ NMR (DMSO-$d_6$, 300 MHz, ppm): δ2.84 (br m, 2H), 3.21 (br dd, 1H), 3.73 (br d, 1H), 3.90 (br d, 1H) 4.29 and 4.38 (minor and major br d, 1H total), 4.98 (br m, 1H), 5.04 (s, 2H), 5.54, 5.60 (minor and major s, 1H total ), 7.15–7.4 (m, 15H).

EXAMPLE 2

(±)-4-[(3,4-Dimethoxyphenyl)acetyl]-1-(diphenylacetyl)-2-piperazinecarboxylic acid Step A: (±)-1-(Diphenylacetyl)-2-piperazinecarboxylic acid A mixture of 1.00 g (2.18 mmole) of (±)-4-(benzyloxycarbonyl)-1-(diphenylacetyl)-2-piperazinecarboxylic acid (from Example 1), 500 mg of 10% palladium on carbon, and 10 ml of glacial acetic acid was shaken with hydrogen (initial pressure 48 psig) on a Parr apparatus for 44 hours, by which time TLC (90:10:1 $CHCl_3$—MeOH—$H_2O$) indicated complete reaction. The mixture was filtered through Celite (under $N_2$), and the filter cake was washed with some additional acetic acid. The combined filtrate and washings were evaporated under a stream of $N_2$. The residual gum was dissolved in 10 ml of methanol, and the hazy solution was filtered through Celite. The filter cake was washed with an additional 10 ml of methanol (added to original filtrate). The product was induced to crystallize from the filtrate. After refrigeration for 2 or 3 hours, the crystallized solid was collected on a filter and washed with small volumes of methanol and then with ether to give, after drying, 632 mg (89%) of white crystals, mp 183.5°–185° C. dec.; homogeneous by TLC (4:1:1 BuOH—AcOH—$H_2O$), visualized by UV and by ninhydrin. The $^1H$ NMR was complex, indicating a mixture of rotamers about the amide bond.

Mass spectrum (FAB): m/e 325 (M+1). Analysis ($C_{19}H_{20}N_2O_3$·1.4 $H_2O$): Calculated: C, 65.27; H, 6.57; N, 8.02 Found: C, 65.36; H, 6.68; N, 8.03 $^1H$ NMR (DMSO-$d_6$, 300 MHz, ppm): δ2.28–2.40 (m, ~1H), 2.60 (br t, <1H), 2.75 (dd, <1H), 2.89 (br d, <1H), 2.95–3.2 (m, ~1H), 3.41 (br t, <1H), 3.55 (br t, ~1H), 3.83 (br d, <1H), 4.30 (br d, <1H), 4.40 (br s, <1H), 4.85 (fine d, <1H), 5.39, 5.54 (minor and major s, 1H total), 7.1–7.4 (m, 10H).

Step B: (3,4-Dimethoxyphenyl)acetic acid N-hydroxysuccinimide ester

A mixture of 1.96 g (10 mole) of (3,4-dimethoxyphenyl)acetic acid, 1.15 g (10 mole) of N-hydroxysuccinimide, 2.06 g (10 mmole) of N,N'-dicyclohexylcarbodiimide (DCC) and 20 ml of dry acetonitrile was stirred at ambient temperature in a stoppered flask. Even before all of the starting materials had dissolved, precipitation of N,N'-dicyclohexylurea (DCU) began and soon became heavy, accompanied by a mild exotherm. After 2 days, the DCU was removed by filtration, and the filtrate was concentrated in vacuo. The residual oil was dissolved in a mixture of 40 ml of ether and 10 ml of $CH_2Cl_2$. This solution was shaken with 25 ml of saturated aqueous $NaHCO_3$. The organic phase was dried over $MgSO_4$, diluted with some additional $CH_2Cl_2$ to prevent crystallization, and filtered. Concentration of the filtrate gave a residual semi-solid, which was triturated thoroughly with ether until full crystallization had occurred. The solid was collected on a filter, washed with small volumes of ether, and dried to yield 2.30 g (78%) of light cream-colored crystals, mp 107.5°–108.5° C.; satisfactory purity by TLC in 1:1 hexane-EtOAc.

$^1H$ NMR (CDCl$_3$, 300 MHz, ppm): δ2.81 (s, 4H), 3.85, 3.88 (s, 8H total), 6.8–6.9 (m, 3H).

Step C: (±)-4-[(3,4-Dimethoxyphenyl)acetyl]-1-(diphenylacetyl)-2-piperazinecarboxylic acid A mixture of 162 mg (0.5 mmole) of (±)-1-(diphenylacetyl)-2-piperazinecarboxylic acid (from Step A), 146 mg (0.5 mmole) of (3,4-dimethoxyphenyl)acetic acid N-hydroxysuccinimide ester (from Step B), 69.6 μl (50.5 mg; 0.5 mmole) of triethylamine, and 0.5 ml of dry N,N-dimethylformamide (DMF) was stirred at room temperature in a stoppered flask for 88 hours. The solution was then diluted with 10 ml of ethyl acetate and washed with 4×25 ml of dilute HCl. Because some precipitation had occurred during the washings, additional ethyl acetate and a few ml of tetrahydrofuran (THF) were added. However, the precipitate did not redissolve. The organic layer was separated, dried briefly over $MgSO_4$, and filtered. Concentration of the filtrate gave a residue which solidified upon trituration with a small volume of methanol. The solid was collected on a filter and washed with small volumes of methanol, then with ether. After drying, the yield of white powder was 162 mg (64%), mp 191°–192° C. dec.; homogeneous by TLC in 90:10:1 $CH_2Cl_2$—MeOH—AcOH. The $^1H$ NMR spectrum indicated a complex mixture of rotameric forms.

Mass spectrum (FAB): m/e 503 (M+1). Analysis ($C_{29}H_{30}N_2O_6$·0.33 $H_2O$): Calculated: C, 68.49; H, 6.08; N, 5.51 Found: C, 68.58; H, 6.26; N, 5.28 $^1H$ NMR (DMSO-$d_6$, 300 MHz, ppm): δ2.5–5.1 (complex series of m's, 15H total, including prominent overlapping OCH$_3$ singlets centered at 3.71), 5.5–5.65 (m, 1H), 6.6–6.9 (m, 3H), 7.15–7.35 (m, 10H).

EXAMPLE 3

(±)-4-(Dipentylcarbamoyl)-1-(diphenylacetyl)piperazine-2-carboxylic acid

Step A: Dipentylcarbamoyl chloride

A mixture of 7.86 g (50.0 mmole) of dipentylamine, 18.05 ml (50.0 mmole) of 2.77M NaOH solution and 60 ml of toluene was vigorously stirred at −7° to −5° C., and 60 ml (115.8 mmole) of 1.93 M phosgene in toluene was added dropwise over 1 hour. After stirring an additional 30 min., the cold mixture was separated and the toluene layer was dried over solid NaCl. After filtering, nitrogen was bubbled through the solution for 1 hour and the solution was concentrated in vacuo to 10.5 g. (95%) of light yellow oil.

IR (cm$^{-1}$): 1740

Mass spectrum (FAB); m/e 220 (M+1) $^1H$ NMR (CDCl$_3$, 400 MHz, ppm): δ0.91 (overlapping t, 6H), 1.25–1.38 (m, 2H), 1.53–1.67 (m, 4H), 3.32 (t, 2H), 3.37 (t, 2H).

Step B: (±)-4-(Dipentylcarbamoyl)-1-(diphenylacetyl)-piperazine-2-carboxylic acid A mixture of 79 mg (0.24 mmole) of (±)-1-(diphenylacetyl)piperazine-2-carboxylic acid (from Example 2, Step A) and 2 ml of THF was treated with 49 mg (0.48 mmole) of triethylamine to give a solution which was cooled to 0° C. With stirring a solution of 61 mg (0.25 mmole) of dipentylcarbamoyl chloride (from Step A) in 0.5 ml of THF was added and the solution was briefly warmed to 50° C. and then stirred at 25° C. for 16 hours. The resulting mixture was filtered and the filtrate was concentrated in vacuo to an oil which was dissolved in 0.5 ml of methanol and was chromatographed over an 85×0.9 cm. LH-20 column with 1.7 ml fractions of methanol. Fractions 21–25 were combined and concentrated in vacuo to 70 mg (57%) of oil.

Mass spectrum (FAB): m/e 508 (M+1) $^1H$ NMR (CDCl$_3$, 300 MHz, ppm): δ0.84 (t, 6H), 1.15–1.35 (m, 8H), 1.38–1.55 (m, 4H), 2.6 (m, 1H), 3.1 (m, 6H), 3.35 (m, 1H), 3.42 (m, 1H), 3.7 (m, 1H), 3.92 and 4.05 (minor and major d, 1H total), 5.17 and 5.21 (minor and major s, 1H), 7.2–7.4 (m, 10H).

EXAMPLE 4

Methyl (±)-4-(Dipentylcarbamoyl)-1-(diphenylacetyl) piperazine-2-carboxylate

A solution of 23.4 mg (0.046 mole) of (±)-4-(dipentylcarbamoyl)-1-(diphenylacetyl)piperazine-2carboxylic acid (from Example 3) in a 1:1 mixture of methanol-diethyl ether was cooled to 0° C. with stirring and was treated in a slow stream with 10 ml of ethereal diazomethane which was generated by adding 0.5 g (4.85 mmole) of N-nitrosomethylurea to a mixture of 1.15 g (17.4 mmole) of 85% potassium hydroxide in 1.0 ml of water and 12.5 ml of diethylether at 0° C. The diazomethane slurry was stirred briskly for 10 minutes and the yellow ether solution was dried over 1 g of potassium hydroxide pellets prior to addition to the carboxylic acid solution. The resulting yellow solution of the carboxylic acid and diazomethane was allowed to warm to 25° C. over 16 hours. Evaporation of the solution gave 24 mg (~100%) of pale yellow oil which was homogeneous by TLC (3:1 hexane-ethyl acetate, $R_f$=0.2).

Mass spectrum (FAB): m/e 522 (M+1) $^1$H NMR (CDCl$_3$, 300 MHz, ppm): δ0.85 (t, 6H), 1.20 (m, 4H), 1.26 (m, 4H), 1.43 (m, 4H), 2.58 (t of d, 1H), 2.98 (t of d, 1H), 3.10 (m, 5H), 3.29 (d, 1H), 3.42 (t of d, 1H), 3.68 (s, 3H) overlapping with 3.68 (m, 1H), 3.84 and 3.99 (minor and major d, 1H total), 5.02 and 5.23 (minor s and major s, 1 H total), 7.2–7.3 (m, 10H).

EXAMPLE 5

(±)-4-(Dipentylcarbamoyl)-1-(diphenylcarbamoyl)piperazine-2-carboxylic acid

Step A: (±)-4-(Benzyloxycarbonyl)-1-(diphenylcarbamoyl)piperazine-2-carboxylic acid A mixture of 264 mg (1.00 mmole) of (±)-4-(benzyloxycarbonyl)piperazine-2-carboxylic acid (see Example 1), 202 mg (2.00 mmole) of triethylamine and 3 ml of THF was cooled to 0° C., and with stirring 231 mg (1.00 mole) of diphenylcarbamoyl chloride was added. The mixture was stirred at 25° C. for 16 hours and was concentrated in vacuo. After partitioning between 20 ml of 1N HCl and 30 ml of ethyl acetate the organic phase was dried over sodium sulfate and was concentrated in vacuo to a waxy solid which was chromatographed over an 85×2.5 cm LH 20 column with 11 ml fractions of methanol. Fractions 36–39 were combined and concentrated to 109 mg (24%) of oil which was homogeneous by TLC (ethyl acetate, $R_f$=0.08).

Mass spectrum (FAB): m/e 460 (M+1) Analysis, (C$_{26}$H$_{25}$N$_3$O$_5$.0.5 H$_2$O): Calculated: C, 66.59; H, 5.55; N, 8.96 Found: C, 66.90; H, 5.63; N, 8.47. $^1$H NMR (CDCl$_3$, 300 MHz, ppm): δ2.6–2.8 (m, 1H), 3.04 (d of d, 1H), 3.21 (m, 1H), 3.63 (d, 1H), 3.83 (m, 1H), 4.56 (d, 1H), 4.76 (s, 1H), 5.12 (s, 2H), 7.08–7.22 (m, 5H), 7.24–7.39 (m, 10H).

Step B: (±)-1-(Diphenylcarbamoyl)piperazine-2-carboxylic acid acetate salt

A solution of 109 mg. (0.24 mmole) of (±)-4-(benzyloxycarbonyl)-1-(diphenylcarbamoyl)piperazine-2carboxylic acid (from Step A) in 3 ml of methanol containing 3 drops of acetic acid and 50 mg of 10% Pd/C was hydrogenated with rocking at 40 psi of hydrogen for 16 hours. The mixture was filtered through Celite and the solution was concentrated in vacuo to 66 mg (71%) of solid which was homogeneous by TLC (1:1:1:1 n-butyl alcohol-acetic acid-water-ethyl acetate, $R_f$=0.70). $^1$H NMR (CDCl$_3$, 300 MHz, ppm): δ2.05 (s, 3H), 2.72 (m, 1H), 2.96 (m, 1H), 3.12 (m, 1H), 3.26 (m, 1H), 3.67 (m, 1H), 3.79 (m, 1H), 4.78 (br.s, 1H), 7.0–7.3 (m, 10H).

Step C: (±)-4-(Dipentylcarbamoyl)-1-(diphenylcarbamoyl)-piperazine-2-carbocyclic acid A solution of 66 mg (0.17 mmole) of (±)-1-diphenylcarbamoyl)piperazine-2-carboxylic acid acetate salt (from Step B) and 100 mg (0.99 mmole) of triethylamine in 2 ml of THF was treated with 1 ml of water to dissolve the precipitated salts and was treated with 50 mg (0.23 mmole) of dipentylcarbamoyl chloride (from Example 3, Step A) in 0.3 ml. of THF. The solution was warmed at 50° C. for 16 hours. After concentrating in vacuo, the residue was partitioned between 20 ml of 0.1N HCl and 30 ml. of ethyl acetate. The organic phase was dried over sodium sulfate and concentrated to 83 mg. (96%) of pale yellow oil.

Mass spectrum (FAB): m/e 509 (M+1) $^1$H NMR (CDCl$_3$, 300 MHz, ppm): δ0.88 (t, 6H), 1.27 (m, 8H), 1.48 (m, 4H), 2.67 (m, 1H), 2.91 (d of d, 1H), 3.05 (m, 5H), 3.29 (br.d, 1H), 3.68 (br.d, 1H), 3.92 (br.d, 1H), 4.74 (br.s, 1H), 7.1–7.4 (m, 10H).

EXAMPLE 6

Methyl (±)-4-(Dipentylcarbamoyl)-1-(diphenylcarbamoyl)-piperazine,2-carboxylate

A solution of 22.6 mg (0.044 mmole) of (±)-4-(dipentylcarbamoyl)-1-(diphenylcarbamoyl)piperazine-2-carboxylic acid (from Example 5) in 2 ml of diethyl ether was treated with diazomethane according to the procedure described in Example 4. A quantitative yield of 23 mg of pale yellow oil was obtained which was homogeneous by TLC (3:1 hexane-ethyl acetate, $R_f$=0.15).

Mass spectrum (FAB): m/e 523 (M+1) $^1$H NMR (CDCl$_3$, 300 MHz, ppm): δ0.85 (t, 6H), 1.2–1.35 (m, 8H), 1.47 (m, 4H), 2.62 (m, 1H), 2.88 (m, 1H), 3.0–3.3 (m, 6H), 3.68 (m, 1H), 3.73 (s, 3H), 3.84 (d, 1H), 4.77 (s, 1H), 7.05–7.35 (m, 10H).

EXAMPLE 7

(S)-4-(Dipentylcarbamoyl)-1-(diphenylcarbamoyl)piperazine-2-carboxylic acid

Step A: (S)-4-(Benzyloxycarbonyl)piperazine-2-carboxylic acid

A solution of 16.4 g (27.6 mmole) of (S)-piperazine-2-carboxylic acid.2 camphorsulfonic acid [E. Felder, S. Maffei, S. Pietra and D. Pitre, *Helv. Chim, Acta*, 43, 888 (1960)]* in 60 ml of water was treated with 2.0 g (14.9 mmole) of cupric chloride to give a light blue solution. 4.16 g (52 mmole) of 50% sodium hydroxide was added to raise the pH to 9.5 giving a deep blue colored solution. A 60 ml portion of acetone was added and the solution was cooled to 0° C. with mechanical stirring. While at 0°, a solution of 6.0 g (33.4 mmole) of 95% benzyl chloroformate in 28 ml of acetone and 28 ml (28 mmole) of 1N sodium hydroxide were added at equal rates over 2 hours to give a slurry of light blue solid in a deep blue solution. After centrifuging, the solid was stirred with 200 ml of 1:1 ethanol-water and was acidified to pH 3 with 6N HCl. The light blue solution was applied to 200 cc of Dowex 50 (H+) which was washed with 900 ml of 1:1 ethanol-water until no longer acid. The column was washed with 600 ml of 6:97:97 pyridine-ethanol-water, and the product was eluted with 800 ml of the same solvent. The solution was concentrated to 200 ml in vacuo and the slurry was lyophilized to give 5.09 g (70%) of white solid, mp 198°–200° C. dec., homogeneous by TLC (1:1:1:1 n-butyl alcoholacetic acid-water-ethyl acetate, $R_f$=0.75; 80:20:2 chloroform methanol-ammonia water, $R_f$=0.30).

Mass spectrum (FAB): m/e 265 (M+1) $^1$H NMR (DMSO-d$_6$, 400 MHz, ppm): δ2.82 (t of d, 1H), 3.0–3.1 (m, 3H), 3.26 (d of d, 1H), 3.89 (d, 1H), 4.19 (d, 1H), 5.08 (s, 2H), 7.3–7.4 (m, 5H).

*Note: The "(−)-piperazine-2-carboxylic acid" obtained by this literature procedure was converted to its dihydrochloride salt, having [α]$_D$=5.24° (c=1.25, H2H). This is essentially equal and opposite in sign to the rotation reported for (R)-piperazine-2-carboxylic acid dihydrochloride prepared from a chiral starting material of known absolute configuration [B. Aebischer, et al., *Helv. Chim. Acta,* 72, 1043 (1989)]. Thus the configuration of the (−)-piperazine-2-carboxylic acid used here is assigned as (S).

Step B: (S)-4-(Benzyloxycarbonyl)-1-(diphenylcarbamoyl)piperazine-2-carboxylic acid A solution of 1.03 g (3.90 mmole) of (S)-4-(benzyloxycarbonyl)piperazine-2-carboxylic acid (from Step A) in 12 ml. of DMF was treated with 0.788 g (7.79 mmole) of triethylamine at 25° C. With stirring 0.901 g (3.89 mmole) of diphenylcarbamoyl chloride was added in portions over 2 hours. After 16 hours the mixture was concentrated in vacuo to an orange oil which was chromatographed over an 88×2.5 cm LH 20 column with 11 ml. fractions of methanol. Fractions 35–43 were combined and concentrated to 1.136 g (64%) of pale yellow oil which contained a major spot by TLC (80:18:2 chloroform-methanol-ammonia water, $R_f$=0.45).

Mass spectrum (FAB): m/e 460 (M+1) $^1$H NMR (CDCl$_3$, 300 MHz, ppm): δ2.65 (br m, 1H), 3.03 (d of d, 1H), 3.15 (m, 1H), 3.58 (d, 1H), 3.80 (d, 1H), 4.52 (d, 1H), 4.73 (s, 1H), 5.12 (s, 2H), 7.03–7.45 (m, 15H).

Step C: (S)-1-(Diphenylcarbamoyl)piperazine-2-carboxylic acid acetate salt

A solution of 1.136 g (2.47 Mole) of (S)-4-(benzyloxycarbonyl)-1-(diphenylcarbamoyl)piperazine-2-carboxylic acid (from Step B) and 0.5 ml of acetic acid in 10 ml of methanol was treated with 0.50 g of 10% Pd/C, and the mixture was hydrogenated at 40 psi with rocking for 10 hours. The mixture was filtered and the catalyst was washed with 40 ml of acetic acid at 60° C. The organics were combined, concentrated in vacuo and flushed with 3×40 ml of ethyl acetate to give 0.73 g (76%) of white solid which was homogeneous by TLC (1:1:1:1 n-butyl alcohol-acetic acid-water-ethyl acetate, $R_f$=0.70; 80:18:2 chloroform-methanol-ammonia water, $R_f$=0.10).

Mass spectrum (FAB): m/e 326 (M+1) $^1$H NMR (DMSO-d$_6$, 200 MHz, ppm): δ1.90 (s, 3H), 2.9–3.7 (m, 6H), 4.19 (br. s, 1H), 7.02–7.17 (m, 6H), 7.27–7.38 (m, 4H).

Step D: (S)-4-(Dipentylcarbamoyl)-1-(diphenylcarbamoyl)piperazine-2-carboxylic acid A mixture of 0.73 g (2.05 mmole) of (S)-1-(diphenylcarbamoyl)piperazine-2-carboxylic acid acetate salt (from Step C) and 0.59 g (5.83 mmole) of triethylamine in 15 ml of DMF was treated with dipentylcarbamoyl chloride (from Example 3, Step A) under nitrogen at 50° C. with stirring for 2 hours to give a clear solution. The DMF was removed in vacuo over a 50° C. bath to leave a yellow oil which was partitioned between 100 ml of 0.2N HCl and 125 ml of ethyl acetate. After drying over sodium sulfate the ethyl acetate was removed in vacuo to leave a dark yellow, gummy material which was flash chromatographed over 100 cc of silica gel with 16×15 ml fractions of 1:1 (hexane:ethyl acetate) and with 15 ml fractions of methanol. Methanol fractions 5–11 were combined and concentrated. The residue was applied to an 85×2.5 cm LH-20 column and eluted with 11 ml fractions of methanol. Fractions 33–38 were combined, concentrated and rechromatographed over LH-20 exactly as before. Fractions 33–39 were combined and concentrated to 124 mg (12%) of glassy gum, homogeneous by TLC (80:20:2 chloroform-methanol-ammonia water, $R_f$=0.5).

Mass spectrum (FAB): m/e 509 (M+1) Analysis (C$_{29}$H$_{40}$N$_4$O$_4$.0.4 H$_2$O): Calculated: C, 67.45; H, 7.91; N, 10.85 Found: C, 67.70; H, 8.03; N, 10.65 $^1$H NMR (CDCl$_3$, 400 MHz, ppm): δ0.85 (t, 6H), 1.19 (m, 4H), 1.27 (m, 4H), 1.46 (m, 4H), 2.63 (t of d, 1H), 2.91 (d of d, 1H), 3.11 (m, 5H), 3.23 (m, 1H), 3.62 (m, 1H), 3.89 (d, 1H), 4.72 (s, 1H), 7.11 (d, 4H), 7.14 (t, 2H), 7.29 (t, 4H).

EXAMPLE 8

Methyl (S)-4-(dipentylcarbamoyl)-1-(diphenylcarbamoyl)piperazine-2-carboxylate

Following the procedure of Examples 4 and 6 above, 238 mg (0.468 mmole) of (S)-4-(dipentylcarbamoyl)-1-(diphenylcarbamoyl)piperazine-2-carboxylic acid (from Example 7) and diazomethane in 10 ml of methanol-ether (1:1), gave a quantitative yield of methyl (S)-4-(dipentylcarbamoyl)-1-(diphenylcarbamoyl)piperazine-2-carboxylate. TLC: $R_f$ 0.85 [Analtech SGF plate developed with isoamyl alcohol-acetone-water (5:2:1)].

Mass spectrum (FAB): m/e 523 (M+1) $^1$H NMR (CDCl$_3$, 400 MHz, ppm): δ0.86 (t, 6H), 1.19 (m, 4H), 1.26 (m, 4H), 1.43 (m, 4H), 2.61 (br.t, 1H), 2.88 (m, 1H), 2.99–3.18 (2m, 4H), 3.22 (m, 1H), 3.28 (m, 1H), 3.67 (m, 1H), 3.72 (s, 3H), 3.84 (d, 1H), 4.78 (br.s, 1H), 7.08 (d, 4H), 7.13 (t, 2H), 7.29–7.32 (t, 4H).

EXAMPLE 9

(S)-4-(Dipentylcarbamoyl)-1-(diphenylacetyl)piperazine-2-carboxylic acid

Step A: (S)-4-(Benzyloxycarbonyl)-1-(diphenylacetyl)-piperazine-2-carboxylic acid A solution of 1.00 g (3.78 mole) of (S)-4-(benzyloxycarbonyl)piperazine-2-carboxylic acid (from Example 7, Step A) in 10 ml of DMF at 25° C. was treated with 0.755 g. (7.46 mmole) of triethylamine. The solution was cooled to 0° C. and 0.95 g (4.12 mmole) of diphenylacetyl chloride was added in portions over 2 hours. The solution was stirred at 25° C. for 64 hours, concentrated in vacuo and partitioned between 60 ml. of 1N HCl and 60 ml of ethyl acetate. The ethyl acetate was dried over sodium sulfate, concentrated in vacuo and chromatographed in two portions over an 85×2.5 cm LH-20 column with 11 ml fractions of methanol. Fractions 38–41 from both columns were combined and concentrated in vacuo to 785 mg (44%) of oil which was homogeneous by TLC (80:20:2 chloroform-methanol-ammonia water, $R_f$=0.40).

Mass spectrum (FAB): m/e 459 (M+1) $^1$H NMR (CDCl$_3$, 400 MHz, ppm): δ2.68 (m, 1H), 3.16 (m, 1H), 3.38 (m, 1H), 3.72 (m, 1H), 3.88 (m, 1H), 4.51 (m, 1H), 4.66 (d, 1H), 5.21 (s, 1H), 7.17–7.35 (m, 15H).

Step B: (S)-1-(Diphenylacetyl)piperazine-2-carboxylic acid acetate salt

A solution of 785 mg (1.71 mmole) of (S)-4-(benzyloxycarbonyl)-1-(diphenylacetyl)piperazine-2carboxylic acid (from Step A) in 25 ml of methanol was treated with 800 mg of 10% Pd/C and the mixture was hydrogenated at 40 psi at 25° C. with rocking for 4 hours. The mixture was filtered and the catalyst was washed with 4×30 ml of acetic acid. All organic phases were combined, concentrated in vacuo, redissolved in 100 ml of water and reconcentrated in vacuo to leave 404 mg (73%) of waxy solid which was homogeneous by TLC (4:1:1 n-butyl alcohol-acetic acid-water, $R_f$=0.55).

Mass spectrum (FAB): m/e 325 (M+1) $^1$H NMR (CD$_3$OD, 400 MHz, ppm): δ1.98 (s, 3H), 2.39 (m, 1H), 2.91 (t of d, 1H), 3.02 (m, 1H), 3.15 (m, 1H), 3.55 (m, 1H), 3.84 and 4.03 (two d, 1H total), 4.61 (m, 1H), 5.52 (d, 1H), 7.15–7.42 (m, 10H).

Step C: (S)-4-(Dipentylcarbamoyl)-1-(diphenylacetyl)-piperazine-2-carboxylic acid A solution of 404 mg (1.05 mmole) of (S)-1-(diphenylacetyl)piperazine-2-carboxylic acid acetate salt (from Step B) and 483 mg (3.74 mmole) of N,N-diisopropylethylamine in 8 ml of DMF at 0° C. was treated with stirring under nitrogen with 273 mg. (1.25 mmole) of dipentylcarbamoyl chloride (from Example 3, Step A). The solution was stirred at 25° C. for 16 hours and was concentrated in vacuo. The residue was partitioned between 20 ml of 1N HCl and 50 ml. of chloroform. The chloroform phase was dried over sodium sulfate and concentrated to a yellow oil which was chromatographed in two parts over an 85×2.5 cm LH-20 column with 10 ml. fractions of methanol. Fractions 31–34 were combined from each and concentrated in vacuo to give 404 mg (76%) of pale colored oil which was homogeneous by TLC (80:20:2 chloroform-methanol-ammonia water, R$_f$=0.55).

Mass spectrum (FAB): m/e 508 (M+1) $^1$H NMR (CDCl$_3$, 400 MHz, ppm): δ0.86 (m, 6H), 1.18 (m, 4H), 1.24 (m, 4H), 1.46 (m, 4H), 2.58 (t of d, 1H), 2.94 (m, 1H), 3.10 (m, 4H), 3.32 (br.d, 1H), 3.38 (m, 1H), 3.71 (m, 1H), 3.94 and 4.04 (minor d and major d, 1H total), 4.43 (d, 1H), 5.22 (s, 1H), 7.17–7.37 (m, 10H).

EXAMPLE 10

Methyl (S)-4-(Dipentylcarbamoyl)-1-(diphenylacetyl)-piperazine-2-carboxylate

A solution of 368 mg (0.725 mmole) of (S)-4-(dipentylcarbamoyl)-1-(diphenylacetyl)piperazine-2carboxylic acid (from Example 9) in 5 ml of methanol was treated at 0° C. with 20 ml of diazomethane solution in diethyl ether (prepared by the procedure above). The solution was stirred at 0° C. for 30 minutes and at 25° C. for 30 minutes. The excess diazomethane was destroyed by the dropwise addition of acetic acid until the solution became colorless. The resulting solution was concentrated in vacuo and the residue was chromatographed over an 85×2.5 cm LH-20 column and concentrated in vacuo to 225 mg (59%) of pale colored oil which was homogeneous by TLC (1:1 hexane-ethyl acetate, R$_f$=0.7).

Mass spectrum (FAB): m/e 522 (M+1) $^1$H NMR (CDCl$_3$, 400 MHz, ppm): δ0.87 (t, 6H), 1.16 (m, 4H), 1.27 (m, 4H), 1.43 (m, 4H), 2.58 (t of d, 1H), 2.97–3.16 (m, 5H), 3.28 (d of d, 1H), 3.42 (t of d, 1H), 3.47 (d, 1H), 3.70 (s, 3H), 3.73 (d, 1H), 3.83 and 3.99 (minor d and major d, 1H total), 5.01 and 5.23 (minor s and major s, 1H total), 7.20–7.35 (m, 10H).

EXAMPLE 11

(S)-1-(N-Pentyl-N-phenylcarbamoyl)-4-(diphenylcarbamoyl)piperazine-2-carboxylic acid Step A: N-Pentylaniline A solution of 22.6 g (200 mmole) of aniline and 51.7 g (600 mmole) of valeraldehyde in 200 ml of ethanol was treated with stirring under nitrogen at 25° C. with a solution of 12.57 g (200 mmole) of sodium cyanoborohydride in 100 ml of ethanol which was added with a syringe pump over 24 hours. The reaction mixture was added dropwise to 500 ml of 2N HCl. The solution was concentrated to 200 ml and then shaken with 300 ml of ethyl acetate. The organic phase was extracted with 300 ml of 1N HCl, and the combined acidic layers were added dropwise to an excess of 1N NaOH to leave a basic solution and an oil which were extracted with 150 ml of ethyl acetate. Concentration gave 28 g of oil which was vacuum distilled. The fractions distilling at 1.5 mm of pressure from 80°–95° C. were collected to give 4.05 g (12%) of light yellow oil which was homogeneous by TLC (10:1 hexane-ethyl acetate, R$_f$=0.45).

$^1$H NMR (CDCl$_3$, 400 MHz, ppm): δ0.89 (t, 3H), 1.33 (m, 4H), 1.60 (m, 2H), 3.08 (t, 2H), 6.59 (d, 2H), 6.67 (t, 1H), 7.16 (t, 2H).

Step B: N-Pentyl-N-phenylcarbamoyl chloride

A solution of 4.05 g (24.8 mmole) of N-pentylaniline (from Step A) in 45 ml of toluene and 8.96 ml (24.8 mmole) of 2.77N NaOH were mechanically stirred at −5° C., and 25.7 ml (49.6 mmole) of 1.93M phosgene in toluene was added dropwise over 30 minutes while maintaining −5°. After half the phosgene solution had been added, the rate of addition was increased easily. After stirring at −5° for an additional 30 minutes, the phases were separated and the toluene layer was dried over 10 g of solid sodium chloride. Concentration gave 5.5 g (98%) of dark yellow oil.

$^1$H NMR (CDCl$_3$, 400 MHz, ppm): δ0.87 (t, 3H), 1.27 (m, 4H), 1.58 (m, 2H), 3.69 (t, 2H), 7.20 (d, 2H), 7.38 (m, 3H).

Step C: (S)-4-(Diphenylcarbamoyl)piperazine-2-carboxylic acid acetate Salt

A stirred solution of 6.0 g (10.1 mmole) of (S)-piperazine-2-carboxylic acid•2 camphorsulfonic acid (see Example 7, Step A, for reference) in 20 ml of water was treated with a solution of 3.8 g (28.3 mmol) of cupric chloride in 20 ml of water and the pH of the resulting solution was increased to 9.5 with 50% sodium hydroxide. The deep blue solution was cooled to 0 to −5° C. and 40 ml of acetone was added. Over 1 hour a solution of 2.38 g (10.27 mmole) of diphenylcarbamoyl chloride in 10 ml of acetone and 10.1 ml of 1N sodium hydroxide were added dropwise with vigorous stirring, and the mixture was stirred at 0° C. for 1 hour and at 25° C. for 1 hour. The filtered solid was washed with 20 ml portions of water, ethanol and diethyl ether to leave 5.02 g of a pale blue solid. The solid was dissolved in a mixture of 60 ml of acetic acid and 20 ml of water. The mixture was warmed to 80° C. and hydrogen sulfide was bubbled through it for 1 hour with vigorous stirring. The mixture was cooled to 25° C. and the excess hydrogen sulfide was displaced with a stream of nitrogen for 16 hours. The mixture was filtered and the black sulfide was washed with 20 ml of 3:1 acetic acid-water. The combined filtrate and washings were concentrated in vacuo to 3.04 g (7.9 mmole, 79%) of foam which was homogeneous by TLC (5:1:1:1 ethyl acetate-acetic acid-water-n-butyl alcohol, R$_f$=0.3).

Mass spectrum (FAB): m/e 326 (M+1)

Step D: (S)-1-(N-Pentyl-N-phenylcarbamoyl)-4-(diphenylcarbamoyl)piperazine-2-carboxylic acid A stirred solution of 0.383 g (1.00 mmole) of (S)-4-(diphenylcarbamoyl)piperazine-2-carboxylic acid acetate salt (from Step C) and 0.400 g (3.09 mmole) of N,N-diisopropylethylamine in 6 ml of DMF at 0° C. was treated with 0.253 g (1.12 mmole) of N-pentyl-N-phenylcarbamoyl chloride (from Step B) and then was warmed to 25° C. for 16 hours. The DMF was removed in vacuo and the residue was partitioned between 20 ml of 1N HCl and 50 ml of chloroform which was dried over sodium sulfate and concentrated in vacuo to a yellow oil. The oil was flash chromatographed over 100 cc of silica gel with 12×25 ml of chloroform, 10×25 ml of 80:20:2 chloroform-methanol-ammonia water. Fractions 19–26 were combined and concentrated to 0.338 g (ammonium salt) of clear glass which was homogeneous by TLC (80:20:2 chloroform-methanol-ammonia water, $R_f$=0.4). The product was partitioned between 20 ml. of 1N HCl and 30 ml of chloroform which was dried over sodium sulfate and concentrated in vacuo to 0.337 g (72%) of a clear glass.

Mass spectrum (FAB): m/e 515 (M+1) $^1H$ NMR (CDCl$_3$, 400 MHz, ppm): δ0.82 (t, 3H), 1.22 (m, 4H), 1.46 (m, 1H), 1.59 (m, 1H), 2.29 (m, 1H), 2.77 (m, 2H), 2.96 (m, 1H), 3.39 (d, 1H), 3.52 (m, 1H), 3.71 (m, 1H), 4.19 (d, 1H), 4.35 (s, 1H), 7.03–7.12 (m, 8H), 7.22–7.27 (m, 5H), 7.37 (t, 2H).

EXAMPLE 12

(±)-1,4-Bis(diphenylcarbamoyl)piperazine-2-carboxylic acid

A solution of 946 mg (4 mmole) of 98% diphenylcarbamoyl chloride in 4 ml of acetonitrile was added dropwise to a stirring solution of 406.2 mg (2 mmole) of piperazine-2-carboxylic acid dihydrochloride [E. Felder, S. Maffei, S. Pietra and D. Pitre, *Helv. Chim. Acta*, 43, 888 (1960)] in 4 ml of 2.5N sodium hydroxide at a temperature between 0° and 5° C. After the addition was completed, the stirring was continued for 4 hours and the solution was acidified with 2N hydrochloric acid while cooling in an ice bath. The reaction mixture was concentrated under reduced pressure and the residue was extracted with chloroform. After washing with water, the chloroform solution was dried over MgSO$_4$ and concentrated in vacuo. The only product which solidified on cooling was triturated with isopropyl ether to give 270 mg (26%) of (±)-1,4-bis-(diphenylcarbamoyl)piperazine-2-carboxylic acid, m.p. 244°–246° C.

Mass spectrum (FAB): m/e 521 (M+1) Analysis (C$_{31}$H$_{28}$N$_4$O$_4$): Calculated: C, 71.02; H, 5.42; N, 10.76 Found: C, 71.08; H, 5.37; N, 10.26. $^1$N NMR (CDCl$_3$, with 2 drops CD$_3$OD, 400 MHz, ppm): δ2.58 (t of d, 1H), 2.69 (br.d, 1H), 2.9–3.0 (under methanol, about 1H), 3.39 (d, 1H), 3.64 (d, 1H), 4.20 (d, 1H), 4.51 (s, 1H), 6.92 (d, 4H), 7.01 (d, 4H), 7.08 (t, 2H), 7.20–7.25 (m, 10H).

EXAMPLE 13

1,4-bis(diphenylcarbamoyl)-trans-2,5-dimethylpiperazine

To a stirred solution of diphenylcarbamoyl chloride (2.32 g, 10 mmole) and 1.30 g (10 mmole) of N,N-diisopropylethylamine in 40 ml of chloroform was added 571 mg (5 mmole) of trans-2,5-dimethylpiperazine in 5 ml of chloroform. After stirring for 16 hours at room temperature, the reaction mixture was evaporated under reduced pressure and water added. The chloroform layer was then extracted with 2N HCl and washed with water. After drying and concentrating to dryness, the white solid was triturated with isopropyl ether to yield 835 mg. (33%) of 1,4-bis(diphenylcarbamoyl)-trans-2,5-dimethylpiperazine, m.p. 255°–257° C.

Mass spectrum (FAB): m/e 505 (M+1) Analysis (C$_{32}$H$_{32}$N$_4$O$_2$): Calculated: C, 76.16; H, 6.39; N, 11.10 Found: C, 75.85; H, 6.39; N, 10.83.

EXAMPLE 14

(±)-2-Methyl-1,4-bis(diphenylcarbamoyl)piperazine

This compound was prepared in a manner similar to that of Example 13 From 9.27 g (40 mmole) of diphenylcarbamoyl chloride , 5.17 g (40 mmole) of N,N-diisopropylethylamine and 2 g (20 mmole) of (±)-2-methyl piperazine, 4.16 g (42%) of (±)-2-methyl-1,4-bis(diphenylcarbamoyl)piperazine, m.p. 200°–202° C. was obtained.

Mass spectrum (FAB): m/e 491 (M+1) Analysis (C$_{31}$H$_{30}$N$_4$O$_2$): Calculated: C, 75.89; H, 6.16; N, 11.42 Found: C, 75.59; H, 6.20; N, 11.12.

EXAMPLE 15

(S)-1-[N-(3-bromophenyl)-N-phenylcarbamoyl]-4-(dipentylcarbamoyl)piperazine-2-carboxylic acid Step A: N-(3-Bromophenyl)-N-phenylcarbamoyl-chloride A solution of 15.0 g ( 60.4 mmole ) of 3-bromodiphenylamine [i.e., N-(3-bromophenyl)aniline][S. Kurzepa and J. Cieslak, *Roczniki Chem.*, 34, 111 (1960)] in 30 ml of toluene and 50 ml (116 mmole) of 1.93M phosgene in toluene were combined and heated at 90° C. under nitrogen for 2 hours with stirring. The red-orange colored solution was cooled, flushed with nitrogen for 2 hours to remove excess phosgene and concentrated in vacuo to 18.0 g (58.0 mmole, 96%) of red-orange oil which was homogeneous by TLC (4:1 hexane-ethyl acetate, $R_f$=0.80).

Mass spectrum (FAB): m/e 310 (M+1) IR (neat, cm$^{-1}$): 1740

Step B: (S)-4-(Benzyloxycarbonyl)-1-[N-(3-bromophenyl)-N-phenylcarbamoyl]piperazine-2-carboxylic acid A solution of 2.52 g (9.54 mmole) of (S)-4-(benzyloxycarbonyl)piperazine-2-carboxylic acid (from Example 7, Step A) in 45 ml of DMF was treated dropwise with 4.91 g (38.0 mmole) of N,N-diisopropylethylamine followed by the dropwise addition of 3.03 g (9.76 mmole) of N-(3-bromophenyl)-N-phenylcarbamoyl chloride (from Step A). The resulting solution was stirred under nitrogen at 25° C. for 66 hours. The solution was then concentrated in vacuo to remove excess DMF and base, and the colored syrup was dissolved in 100 ml of diethyl ether. This was extracted with 100 ml and 30 ml portions of 1N HCl and with 30 ml of water. Addition of 75 ml of 5% sodium bicarbonate to the ether solution precipitated an orange oil. After 30 minutes of settling the ether was extracted with a second 50 ml portion of 5% sodium bicarbonate. The aqueous solution and precipitated oil were combined and acidified to pH 1 with 6N HCl. The resulting mixture was extracted with 2×100 ml of methylene chloride. The methylene chloride extracts were combined and concentrated in vacuo without drying to give 4.06 g (7.54 mmole, 79%) of foam, homogeneous by TLC (1:1:1:1 n-butyl alcohol-acetic acid-ethyl acetate-water, $R_f$=0.95, and 80:20:2 chloroform-methanol-ammonium hydroxide, $R_f$=0.48).

Mass spectrum (FAB): m/e 538 (M+1) $^1H$ NMR (CDCl$_3$, 400 MHz, ppm): δ2.70 (br.s, 1H), 3.06 (d, 1H), 3.17 (t, 1H), 3.57 (d, 1H), 3.85 (br.m, 1H), 4.56 (d, 1H), 4.77 (s, 1H), 5.10 (d, 2H), 7.00–7.38 (m, 14H).

Step C: (S)-1-[N-(3-Bromophenyl)-N-phenylcarbamoyl]-piperazine-2-carboxylic acid A 2.13 g (3.96 mmole) portion of (S)-4-(benzyloxycarbonyl)-1-[N-(3-bromophenyl-N-phenylcarbamoyl]-piperazine-2-carboxylic acid (from Step B) was dissolved in 40 ml of 30% HBr in acetic acid. After stirring for 1 hour at 25° C., the solution was flushed with nitrogen to remove the excess of HBr. Concentration in vacuo gave an oily residue which was partitioned between 100 ml of methylene chloride and 100 ml of water. The stirred slurry was neutralized to pH 7 with 10% NaOH solution. After a brief stirring the entire mixture was filtered to collect 1.50 g (3.71 mmole, 94%) of white solid which was homogeneous by TLC (5:1:1:1 ethyl acetate-n-butyl alcohol-ethyl acetate-water $R_f=0.33$).

Mass spectrum (FAB): m/e 404 (M+1) $^1$H NMR (DMSO-d$_6$, 400 MHz, ppm): δ2.58 (br.t, 1H), 2.95 (d, 1H), 3.15 (t of d, 1H), 3.41 (d, 1H), 3.62 (d, 1H), 4.16 (br.s, 1H), 7.00 (d of t, 1H), 7.11 (d, 2H). 7.17 (t, 1H), 7.20–7.28 (m, 3H), 7.35 (t, 2H).

Step D: (S)-1-[N-(3-Bromophenyl)-N-phenylcarbamoyl]-4-(dipentylcarbamoyl)piperazine-2-carboxylic-acid A solution of 1.84 g (3.96 mmole) of (S)-1-[N-(3-bromophenyl)-N-phenylcarbamoyl]piperazine-2-carboxylic acid (from Step C) in 15 ml of DMF was cooled over ice, and 2.07 g (16.0 mmole) of N,N-diisopropylethylamine was added, followed by the dropwise addition of 1.08 g (4.92 mmole) of dipentylcarbamoyl chloride (from Example 3, Step A) in 5 ml of DMF over 1 hour. The solution was warmed, and after stirring 16 hours at 25° C., the solution was concentrated in vacuo. The residue was stirred with 50 ml of 1N HCl which was extracted with 2×50 ml of methylene chloride. After concentration in vacuo the residue was mixed with 100 ml of diethyl ether which was extracted with 4×30 ml of 5% sodium bicarbonate. A tan oil which precipitated was combined with the aqueous solution, and the mixture was acidified to pH 1.0 with 1N HCl. Extraction with 100 ml of chloroform gave 1.03 g (1.76 mmole, 44%) of tan foam which was homogeneous by TLC (80:80:2 chloroform-methanol-ammonium hydroxide, $R_f=0.45$).

Mass spectrum (FAB): m/e 587 (M+1) $^1$H NMR (CDCl$_3$, 400 MHz, ppm): δ0.85 (t, 6H), 1.18 (m, 4H), 1.27 (m, 4H), 1.46 (m, 4H), 2.70 (t of d, 1H), 2.90 (d of d, 1H), 3.10 (m, 5H), 3.26 (d, 1H), 3.61 (d, 1H), 3.94 (d, 1H), 4.71 (s, 1H), 7.05 (d of d, 1H), 7.10–7.26 (m, 6H), 7.33 (t, 2H).

EXAMPLE 16

(S)-1-[N-(3-Chlorophenyl-N-phenylcarbamoyl]-4-(dipentylcarbamoyl)piperazine-2-carboxylic acid Step A: N-(3-Chlorophenyl)-N-phenyl)carbamoyl chloride Following the procedure of Example 15, Step A, 20.4 g (100 mmole) of 3-chlorodiphenylamine [i.e., N-(3-chlorophenyl)aniline] and phosgene in toluene gave 15.4 g (58%) of N-(3-chlorophenyl)-N-phenylcarbamoyl chloride.

Mass spectrum (FAB): m/e 266 (M+1) IR (neat, cm$^{-1}$): 1740, no NH absorption.

Step B: (S)-1-[N-(3-Chlorophenyl)-N-phenylcarbamoyl]-4-(benzyloxycarbonyl)piperazine-2-carboxylic acid A solution of 2.66 g (10 mmole) of N-(3-chlorophenyl)-N-phenylcarbamoyl chloride (from Step A) in 10 ml of chloroform was added dropwise to a stirring solution of 3.24 g (10 mmole) of (S)-4-(benzyloxycarbonyl)piperazine-2-carboxylic acid (from Example 7, Step A), 2.72 g (25 mmole) of chlorotrimethylsilane and 4.91 g (38 mmole) of N,N-diisopropylethylamine in 60 ml of chloroform at 10° C. The reaction mixture was allowed to warm to room temperature and stirring was continued for 60 hours. The reaction mixture was concentrated in vacuo and water and ether were added. The ethereal solution was extracted with 2N HCl and washed with water until neutral. The organic layer was then extracted with saturated sodium bicarbonate. A tan oil which separated was combined with the aqueous solution, and the mixture was acidified with 2N HCl. The resulting mixture was extracted with methylene chloride, and the organic extract was concentrated in vacuo to give 2.80 g (57%) Of white solid, m.p. 100° C. (softened >80° C.); TLC: $R_f$0.60 [Analtech SGF plate developed with isoamyl alcohol-acetone-water (5:2:1)].

Mass spectrum (FAB): m/e 494 (M+1) Analysis (C$_{26}$H$_{24}$N$_3$O$_5$Cl): Calculated: C, 63.22; H, 4.90; N, 8.51 Found: C, 62.98; H, 4,98; N, 8.34

Step C: (S)-1-[N-(3-Chlorophenyl)-N-phenylcarbamoyl]-piperazine-2-carboxylic acid hydrobromide 1.60 g (3.24 mmole) of (S)-1-[N-(3-chlorophenyl)-N-phenylcarbamoyl]-4-(benzyloxycarbonyl)-piperazine-2-carboxylic acid (from Step B) was dissolved in 16 ml of 30% HBr in acetic acid. After stirring for 16 hours at 25° C., the solution was flushed with nitrogen to remove the excess of HBr. Next the solution was concentrated in vacuo and the residue was triturated with ether. The white solids which separated were recrystallized from methanol-ester to give 1.17 g (82%) of the product, mp 185° C. dec.

Mass spectrum (FAB): m/e 360 (M+1) Analysis (C$_{18}$H$_{18}$N$_3$O$_3$Cl.HBr.1.5 H$_2$O): Calculated: C, 46.18; H, 4.70; N, 8.98 Found: C, 46.20; H, 4.35; N, 8.66

Step D: (S)-1-[N-(3-Chlorophenyl)-N-phenylcarbamoyl]-4-(dipentylcarbamoyl)piperazine-2-carboxylic acid To a suspension of 1.05 g (2.3 mmole) of (S)-1-[N-(3-chlorophenyl)-N-phenylcarbamoyl]piperazine-2-carboxylic acid hydrobromide (from Step C) in 20 ml of methylene chloride was added 1.23 g (9.5 mmole) of N,N-diisopropylethylamine followed by the dropwise addition of a solution of 523 mg (2.38 mmole) of dipentylcarbamoyl chloride (from Example 3, Step A) in 5 ml of methylene chloride. After stirring 24 hours at 25° C., the solution was extracted with 2N HCl, then H$_2$O and dried over MgSO$_4$. The dried methylene chloride solution was concentrated in vacuo and the residue was dissolved in isopropyl ether and was diluted with petroleum ether (bp. 30°–60° C.) until cloudy. The oil which precipitated was then decanted, redissolved in isopropanol and concentrated in vacuo to yield 464 mg (36%) of (S)-1-[N-(3-chlorophenyl)-N-phenylcarbamoyl]-4-(dipentylcarbamoyl)piperazine-2-carboxylic acid as a glassy solid; TLC showed a single spot, $R_f$0.75 (Analtech SGF plates developed with isoamyl alcohol:acetone:water [5:2:1]).

Mass spectrum (FAB): m/e 542 (M+1) Analysis (C$_{29}$H$_{39}$N$_4$O$_4$Cl) Calculated: C, 64.13; H, 7.24; N, 10.32 Found: C, 63.70; H, 6.85; N, 10.23. $^1$H NMR (CDCl$_3$, 400 MHz, ppm): δ0.85 (t, 6H), 1.19 (m, 4H), 1.27 (m, 4H), 1.45 (m, 4H), 2.68 (t of d, 1H), 2.91 (d of d, 1H), 3.11 (m, 4H), 3.19 (m, 1H), 3.28 (d, 1H), 3.62 (d, 1H), 3.92 (d, 1H), 4.74 (s, 1H), 6.99 (d, 1H), 7.06–7.13 (m, 4H), 7.19 (m, 2H), 7.33 (t, 2H).

EXAMPLE 17

(S)-1-(10,11-Dihydro-5H-dibenz[b,f]azepine-5-carbonyl-4-(dipentylcarbamoyl)piperazine-2-carboxylic acid Step A: (S)-1-(10,11-Dihydro-5H-dibenz[b,f]azepine-5-carbonyl)-4-(benzyloxycarbonyl)piperazine-2-carboxylic acid Following the procedure of Example 16, Step B, 811 mg (2.5 mmole) of (S)-4-(benzyloxycarbonyl)-piperazine-2-carboxylic acid (from Example 7, Step A) 680 mg (6.26 mmole) of chlorotrimethylsilane, 1.23 g (9.5 mmole) of N,N-diisopropylethylamine and 665 mg (2.5 mmole ) of 97% of 10,11-dihydro-5H-dibenz[b,f]-azepine-5-carbonyl chloride, gave 284 mg (24%) of (S)-1-(10,11-dihydro-5H-dibenz [b,f]azepine-5-carbonyl)-4-(benzyloxycarbonyl)piperazine-2-carboxylic acid, mp 185° C. (softened >90° C.); TLC $R_f$ 0.68 (Antaltech SGF plates developed with isoamyl alcohol:acetone:water [5:2:1]).

Mass spectrum (FAB): m/e 486 (M+1) Analysis ($C_{28}H_{27}N_3O_5$) Calculated: C, 69.26; H, 5.61; N, 8.65 Found: C, 69.03; H, 5.36; N, 8.25.

Step B: (S)-1-(10,11-Dihydro-5H-dibenz[b,f]azepine-5-carbonyl)piperazine-2-carboxylic acid hydrobromide This compound was prepared in a manner similar to the preparation of Example 16, Step C. From 246 mg (0.5 mmole) of (S)-1-(10,11-dihydro-5H-dibenz[b,f]azepine-5-carbonyl)-4-(benzyloxycarbonyl)-piperazine-2-carboxylic acid (from Step A) and 5 ml of 30% HBr in acetic acid, 202 mg (94%) of (S)-1-(10,11-dihydro-5H-dibenz[b,f]azepine-5-carbonyl)piperazine-2-carboxylic acid hydrobromide, mp 180° C. dec., was obtained.

Mass spectrum m/e 352 (M+1) Analysis ($C_{20}H_{21}N_3O_3 \cdot HBr \cdot 2H_2O$) Calculated: C, 51.25; H, 5.55; N, 8.97 Found: C, 51.07; H, 5.48; N, 8.73.

Step C: (S)-1-(10,11-Dihydro-5H-dibenz[b,f]azepine-5-carbonyl)-4-(dipentylcarbamoyl)piperazine-2-carboxylic acid Following the procedure for the preparation of Example 17, Step D, from 183 mg (0.423 mmole) of (S)-1-(10,11-dihydro-5H-dibenz[b,f]azepine-5-carbonyl)-piperazine-2-carboxylic acid hydrobromide (from Step B), 219 mg (0.169 mmole) of N,N-diisopropylethylamine and 112 mg (0.51 mmole) of dipentylcarbamoyl chloride (from Example 3, Step A) gave 107 mg (47%) of (S)-1-(10,11-dihydro-5H-dibenz[b,f]azepine-5-carbonyl)-4-(dipentylcarbamoyl)piperazine-2-carboxylic acid, mp 121°–124° C., TLC $R_f$ 0.75 (Analtech SGF plates developed with isoamyl alcohol:acetone:water[5:2:1]).

Mass spectrum (FAB): m/e 535 (M+1) Analysis ($C_{31}H_{42}N_4O_4 \cdot \frac{1}{2} H_2O$) Calculated: C, 68.42; H, 7.91; N, 10.30 Found: C, 68,68; H, 7.98; N, 10.14. $^1H$ NMR (CDCl$_3$, 400 MHz, ppm): δ0.84 (t, 6H), 1.18 (m, 4H), 1.28 (m, 6H), 1.44 (m, 4H), 1.82 (m, 1H), 2.52 (br. t, 1H), 2.81 (br, 1H), 2.95 (d of d, 1H), 3.07–3.16 (m, 7H), 3.49 (m, 1H), 3.87 (d, 1H), 4.59 (s, 1H), 7.12–7.23 (m, 6H), 7.42 (d, 2H).

EXAMPLE 18

(S)-2-[(3-(N,N-Diethylamino)propyl)aminocarbonyl]-4-(N,N-di-n-pentylcarbamoyl)-1-(N,N-diphenylcarbamoyl)piperazine A mixture of 204 mg (0.4 mmole) of (S)-1-(N,N-diphenylcarbamoyl)-4-(N,N-di-n-pentylcarbamoyl)-piperazine-2-carboxylic acid and 65 mg (0.42 mmole) of HOBt in 5 mL of THF was treated with 93 mg (0.45 mmole) of DCC at 25° C. After being stirred for 30 min, 63 mg (0.48 mmole) of 3-diethylaminopropylamine was added and the mixture was stirred at 25° C. for 16 hours. The white precipitate was filtered off and the filtrate was concentrated in vacuo. The residue was extracted with 20 mL of CH$_2$Cl$_2$, and the extract washed with 10 mL each of water, saturated aqueous sodium bicarbonate, 1N aqueous hydrochloric acid, and saturated aqueous sodium chloride. The organic phase was dried over magnesium sulfate and concentrated in vacuo to give 241 mg (97%) of an oil which was homogeneous by TLC ($R_f$ 0.75; 5:2:1 isoamyl alcohol:acetone:water).

Mass Spectrum (FAB): m/Z 621 (M+H, 100%). $^1H$ NMR (CDCl$_3$, 400 MHz, ppm): δ0.85 (t, 6H), 1.02 (t, 6H), 1.1–1.3 (m, 8H), 1.43 (pentet, 4H), 1.68 (m, 2H), 2.5–2.6 (m, 6H), 2.70 (td, 1H), 2.85 (dd, 1H), 3.0–3.4 (8H), 3.66 (br d, 1H), 3.87 (d, 1H), 4.47 (br s, 1H), 7.05–7.15 (m, 6H), 7.25–7.33 (m, 4H), 7.59 (br s, 1H).

EXAMPLE 19

(S)-2-[(4-(N,N-Diethylamino)butyl)aminocarbonyl]-4-N,N-di-n-pentylcarbamoyl)-1-(N,N-diphenylcarbamoyl)-piperazine A mixture of 42 mg (0.083 mmole) of (S)-1-(N,N-diphenylcarbamoyl)-4-(N,N-di-n-pentyl-carbamoyl)-piperazine-2-carboxylic acid and 12 mg (0.091 mmole) of HOBt in 1 mL CH$_2$Cl$_2$ was cooled to 0° C. under a nitrogen atmosphere and was treated with 22 mg (0.091 mmole) of EDAC. After 5 min the ice bath was removed, and after an additional 30 min stirring at 22° C. 24 mg (0.17 mmole) of 4-diethylaminobutylamine was added and the mixture was stirred at 22° C. for 24 hours. The mixture was purified by flash chromatography on 16 g of silica with 250 mL of 100:8:0.3 CH$_2$Cl$_2$:MeOH: ammonia water to give 42 mg (81%) of an oil.

Mass Spectrum (FAB): m/Z 642 (M+H, 100%), 230 (ClPhN(Ph)CO, 15%), 184 (25%), 167 (10%). $^1H$ NMR (CDCl$_3$, 400 MHz, ppm ): δ0.85 (t, 6H), 0.99 (t, 6H), 1.15–1.3 (m 8H), 1.45 (pentet, 4H), 2.45–2.6 (m, 6H), 2.66 (t, 1H), 2.79 (dd, 1H), 3.0–3.4 (m, 8H), 3.72 (br d, 1H), 3.91 (d, 1H) 4.48 (br s, 1H), 7.0–7.4 (m, 10H).

EXAMPLE 20

(S)-2-[(2-Aminoethyl)aminocarbonyl]-4-(N,N-di-n-pentylcarbamoyl)1-(N,N-diphenylcarbamoyl)piperazine A mixture of 202 mg (0.4 mmole) of (S)-1-(N,N-diphenylcarbamoyl)-4-(N,N-di-n-pentyl-carbamoyl)-piperazine-2-carboxylic acid and 59 mg (0.44 mmole) of HOBt in 4 mL of CH$_2$Cl$_2$ was cooled to 0° C. and was treated with 107 mg (0.56 mmole) of EDAC. After 5 min, the cooling bath was removed and after an additional 30 min, the mixture was cooled to $-33°$ C. and was treated with 398 microliters (5.96 mmole) of ethylenediamine. After 10 min the cooling bath was removed and the mixture stirred at 22° C. for 24 hours. Most of the volatiles were removed by a gentle stream of nitrogen and the residue was purified by flash chromatography on 23 g of silica gel eluting with 1 liter of 100:9:0.4 CH$_2$Cl$_2$:MeOH: ammonia water to give 125 mg (57%) of an oil.

Mass Spectrum (FAB): m/Z 706 (M+matrix, 40%, 551 (M+H, 100%), 196 (60%). $^1H$ NMR (CDCl$_3$, 400 MHz, ppm): δ0.85 (t, 6H), 1.05 (br s, 2H), 1.1–1.3 (m, 8H), 1.45 (pentet, 4H), 2.7–2.85 (m, 4H), 2.9–3.1 (3H), 3.15–3.3 (5H), 3.73 (br d, 1H), 3.97 (d, 1H), 4.50 (s, 1H), 7.1–7.15 (m, 6H), 7.25–7.33 (m, 4H), 7.46 (br t, 1H).

EXAMPLE 21

(S)-1-[N-(3-Chlorophenyl)-N-phenylcarbamoyl]-2-[(3-(N,N-diethylamino)propyl)aminocarbonyl]-4-(N,N-di-n-pentylcarbamoyl)piperazine According to the procedure of Example 19 above, 20 mg (0.037 mmole) of (S)-1-[N-(3-chlorophenyl)-N-phenylcarbamoyl]-4-(N,N-di-n-pentyl-carbamoyl)piperazine-2-carboxylic acid, 6 mg (0.041 mmole) of HOBt, 10 mg (0.052 mmole) of EDAC, and 10 mg (0.074 mmole) of 3-diethylaminopropylamine after purification by flash chromatography on 16 g of silica gel with 100:7:0.2 $CH_2Cl_2$:MeOH: ammonia water provided 17 mg (71%) of an oil.

Mass Spectrum (FAB): m/Z 657 (M+H, 40%), 656 (M+H, 60%), 655 (M+H, 100%), 621 (20%), 452 (15%), 230 (10%). $^1H$ NMR ($CDCl_3$, 400 MHz, ppm): δ0.85 (t, 6H), 1.02 (t, 6H), 1.1–1.3 (m, 8H), 1.44 (pentet, 4H), 1.68 (br pentet, 2H), 2.55 (br s, 6H), 2.76 (t, 1H), 2.86 (dd, 1H), 3.0–3.15 (m, 5H), 3.2–3.4 (m, 3H), 3.66 (br d, 1H), 3.87 (d, 1H), 4.44 (br s, 1H), 7.06 (m, 3H), 7.1–7.25 (m, 4H), 7.34 (t, 2H), 7.78 (br s, 1H).

EXAMPLE 22

(S)-1,4-Bis[N-(3-chlorophenyl)-N-phenylcarbamoyl]-2-[(3-(N,N-diethylamino)propyl)aminocarbonyl]piperazine Step A: (S)1,4-Bis[N-(3-chlorophenyl)-N-phenylcarbamoyl]-2-piperazinecarboxylic acid A suspension of 3.0 g (5 mmole) of (S)-1-(N,N-diphenylcarbamoyl)-4-(N,N-di-n-Pentylcarbamoyl)piperazine-2-carboxylic acid in 50 mL of $CH_2Cl_2$ was treated sucessively with 1.36 g (12.5 mmole) of chlorotrimethylsilane, 2.67 g (30 mmole) of DIEA and 2.67 g (10 mmole) of 3-chlorodiphenylcarbamoyl chloride in 10 mL of $CH_2Cl_2$, and the mixture was stirred at room temperature for 92 hours. The solution was washed with 20 mL of 2N HCl, 15 mL of water (twice) and was concentrated in vacuo. The residue was taken up in ether and insoluble material removed by filtration. The filtrate was washed with water and the light orange solid was filtered and dried to give 987 mg (34%); mp 200°–203° C.; TLC: 5:2:1 Isoamyl alcohol:acetone:water $R_f$ 0.80.

Mass Spectrum (FAB): m/Z 612 (M+Na),589 (M+H). Analysis ($C_{31}H_{26}N_4O_4Cl_2$): Calculated: C,63.16; H,4.45; N,9.50. Found: C,63.20; H,4.48; N,9.41.

Step B: (S)-1,4-Bis[N-(3-chlorophenyl)-N-phenylcarbamoyl]-2-[(3-(N,N-diethylamino)propyl)aminocarbonyl)piperazine According to the procedure of Example 19 above, 20 mg (0.034 mmole) of (S )-1,4-bis[N-(3-chlorophenyl)-N-phenylcarbamoyl]piperazine-2-carboxylic acid, 5 mg (0.037 mmole) of HOBt, 9 mg (0.047 mmole) of EDAC, and 9 mg (0,068 mmole) of 3-diethylamino-propylamine after purification by flash chromatography on 16 g of silica gel with 100:7:0.2 $CH_2Cl_2$: MeOH: ammonia water provided 18 mg (75%) of an oil.

Mass Spectrum (FAB): m/Z 703 (M+H, 5%), 702 (M+H, 15%), 701 (M+H, 45%), 700 (M+H, 100%), 230 (35%). $^1H$ NMR ($CDCl_3$, 400 MHz, ppm): δ1.00 (br s, 6H), 1.70 (br s, 2H), 2.4–2.7 (m, 7H), 2.84 (dd, 1H), 3.04 (br s, 1H), 3.35 (m, 2H), 3.46 (d, 1H), 3.55 (d, 1H), 4.21 (d, 1H), 4.43 (s, 1H), 6.9–7.4 (m, 18H), 7.43 (br s, 1H)

EXAMPLE 23

(S)-1-[N-(3-Chlorophenyl)-N-phenylcarbamoyl]-2-[(4-(N,N-diethylamino)butyl)aminocarbonyl]-4-(N,N-di-n-pentylcarbamoyl)piperazine According to the procedure of Example 19 above, 40 mg (0.074 mmole) of (S)-1-[N-(3-chlorophenyl)-N-phenylcarbamoyl]-4-(N,N-di-n-pentyl-carbamoyl)piperazine-2-carboxylic acid, 11 mg (0.081 mmole) of HOBt, 20 mg (0.103 mmole) of EDAC, and 21 mg (0.147 mmole) of 4-diethylaminobutylamine after purification by flash chromatography on 16 g of silica gel with 100:5:0.2 $CH_2Cl_2$:MeOH: ammonia water provided 38 mg (81%) of an oil.

Mass Spectrum (FAB): m/Z 669 (M+H,100%), 230 (ClPhN(Ph)CO, 20%). $^1H$ NMR ($CDCl_3$, 400 MHz, ppm): δ0.85 (t, 6H), 1.00 (br s, 6H), 1.1–1.35 (m, 8H), 1.4–1.55 (m, 8H), 2.3–2.7 (m, 6H), 2.7–3.05 (m, 5H), 3.1–3.33 (m, 5H), 3.70 (d, 1H), 3.95 (d, 1H), 4.42 (br s, 1H), 7.08 (m, 3H), 7.1–7.3 (m, 4H), 7.34 (t, 2H), 7.52 (br s, 1H).

EXAMPLE 24

(S)-2-[(3-(N,N-Diethylamino)propyl)aminocarbonyl]-4-(N,N-di-n-pentylcarbamoyl)-1-[N-(3-methylphenyl)-N-phenylcarbamoyl]piperazine Step A: N-(3-Methylphenyl)-N-phenylcarbamoyl chloride According to the procedure of Example 15, Step A, 3.66 g (20 mmole) of 3-methyldiphenylamine, 20 mL (38.6 mmole) of 1.93M phosgene is toluene solution, and 20 mL of toluene gave 4.9 g (100%) of a dark solid.

Mass Spectrum (FAB): m/Z 245 (M, 67%), 210 (M-Cl, 100%), 182 (M-COCl, 62%), 167 (M-COCl—$CH_3$, 65%).

Step B: (S)-4-(benzyloxycarbonyl)-1-[N-(3-methylphenyl)-N-phenylcarbamoyl]-piperazine-2-carboxylic acid A mixture of 264 mg (1 mmole) of (S)-4-(benzyloxycarbonyl)piperazine-2-carboxylic acid, 265 mg (1.1 mmole) of N-(3-methylphenyl)-N-phenylcarbamoyl chloride, 390 mg (3 mmole) of DIEA in 5 mL of DMF was stirred for 16 hr at room temperature. The solution was concentrated in vacuo and the residue was taken up in 50 mL of $CH_2CL_2$ and washed with 2×25 mL of 1N HCl. Concentration in vacuo gave 0.55 g of an oil, which was carried on in Step C.

Mass Spectrum (FAB): m/Z 496 (M+Na), 474 (M+1), 210 (MePhN(Ph)CO), 184 (MePhNPh). NMR ($CDCl_3$,400 MHz, ppm): δ2.28 (s,3H), 2.5–2.7 (m, 1H), 3.0–3.2 (m, 2H), 3.55 (m 1H), 3.79 (br s, 1H), 4.53 (br d, 1H), 4.70 (br s, 1H), 5.0–5.15 (m, 2H), 6.8–7.4 (M, 14H).

Step C: (S)-1-[N-(3-methylphenyl)-N-phenylcarbamoyl]-piperazine-2-(S)-carboxylic acid acetate salt A mixture of 0.55 g (ca. 1.17 mmole; crude from Step B above) of (S)-4-(benzyloxylcarbonyl)-1-[N-(3-methylphenyl)-N-phenylcarbamoyl]-piperazine-2carboxylic acid and 10 mL of 30% HBr in acetic acid was stirred overnight at room temperature. The mixture was flushed with nitrogen to remove excess HBr and was then concentrated in vacuo. The product, which partially crystallized over several days, was carried on in Step D.

Step D: (S)-1-[N-(3-methylphenyl)-N-phenylcarbamoyl]-4-(N,N-di-n-pentylcarbamoyl)piperazine-2-carboxylic acid According to the procedure of Example 7, Step D, ca. 1 mmole of (S)-1-[N-(3-methylphenyl)-N-phenylcarbamoyl]-piperazine-2-(S)-carboxylic acid acetate salt (crude from Step C above), 388 mg (3 mmole) of DIEA, 329 mg (1.5 mmole) of N,N-di-n-pentylcarbamoyl chloride in 8 mL of DMF to give 83 mg of an oil.

Mass Spectrum (FAB): m/Z 680 (10%), 567 (M+2Na—H, 30%), 545 (M+Na, 100%), 523 (M+H, 70%), 517 (45%), 362 (M-[CH$_3$(CH$_2$)$_4$]$_2$NCO+Na+H, 45%), 294 (M-[CH$_3$(CH$_2$)$_4$]$_2$NCO—CO$_2$, 40%), 210 (MePhN(Ph)CO, 83%. NMR (CDCl$_3$, 400 MHz, ppm): δ0.80 (m, 6H), 1.1–1.35 (m, 8H), 1.45 (pentet, 4H), 2.29 (s, 3H), 2.66 (t, 1H), 2.8–3.0 (m, 2H), 3.05–3.25 (m, 6H), 3.61 (d, 1H), 3.90 (d, 1H), 4.70 (s, 1H), 6.88–7.00 (m, 3H), 7.05–7.35 (m, 6H).

Step E: (S)-2[(3-(N,N-diethylamino)propyl)aminocarbonyl]-4-(N,N-di-n-pentylcarbamoyl)-1-[N-(3-methylphenyl)-N-phenylcarbamoyl]piperazine According to the procedure of Example 19 above, 26 mg (0.050 mmole) of (S)-1-[N-(3-methylphenyl)-N-phenylcarbamoyl]-4-(N,N-di-n-pentylcarbamoyl)piperazine-2-carboxylic acid, 8 mg (0.055 mmole) of HOBt, 13 mg (0,070 mmole) of EDAC, and 14 mg (0.100 mmole) of 3-diethylaminopropylamine after purification by flash chromatography on 16 g of silica gel with 100:7:0.2 CH$_2$Cl$_2$:MeOH: ammonia water provided 20 mg (62%) of an oil.

Mass Spectrum (FAB): m/Z 636 (~M+H, 100%), 210 (MePhN(CO)Ph, 30%). $^1$H NMR (CDCl$_3$, 400 MHz, ppm): δ0.85 (t, 6H), 1.04 (t, 6H), 1.15–1.35 (t, 8H), 1.44 (pentet, 4H), 1.72 (br s, 2H), 2.28 (s, 3H), 3.5–3.75 (m, 7H), 3.89 (dd, 1H), 3.0–3.30 (m, 7H), 3.34 (m, 1H), 3.66 (d, 1H), 3.89 (d, 1H), 4.48 (br s, 1H), 6.9–7.0 (m, 3H), 7.1–7.35 (m, 6H), 7.55 (br s, 1H).

EXAMPLE 25

(S)-1-[N-(3-Chlorophenyl)-N-phenylcarbamoyl]-2-[(2-(N,N-diethylamino)ethyl)aminocarbonyl]-4-(N,N-di-n-pentylcarbamoyl)piperazine According to the procedure of Example 19 above, 40 mg (0.074 mmole) of (S)-1-[N-(3-chlorophenyl)-N-phenylcarbamoyl]-4-(N,N-di-n-pentylcarbamoyl)piperazine-2-carboxylic acid, 11 mg (0.081 mmole) of HOBt, 20 mg (0.103 mmole) of EDAC, and 21 mg (0.147 mmole) of 2-diethylaminoethylamine after purification by flash chromatography on 16 g of silica gel with 100:5:0.2 CH$_2$Cl$_2$:MeOH: ammonia water provided 38 mg (81%) of an oil.

Mass Spectrum (FAB): m/Z 642 (M+H, 100%), 230 (ClPhN(Ph)CO, 15%), 184 (25%), 167 (10%). $^1$H NMR (CDCl$_3$, 400 MHz, ppm): δ0.85 (t, 6H), 0.99 (t, 6H), 1.15–1.3 (m 8H), 1.45 (pentet, 4H), 2.45–2.6 (6H), 2.66 (t, 1H), 2.79 (dd, 1H), 3.0–3.4 (m, 8H), 3.72 (br d, 1H), 3.91 (d, 1H), 4.48 (br s, 1H), 7.0–7.4 (m, 10H)

EXAMPLE 26

(S)-2-[(2-(N,N-Diethylamino)ethyl)aminocarbonyl]-4-(N,N-di-n-pentylcarbamoyl)-1-(N,N-diphenylcarbamoyl)piperazine According to the procedure of Example 19 above, 40 mg (0.079 mmole) of (S)-1-(N,N-diphenylcarbamoyl)-4-(N,N-di-n-pentylcarbamoyl)piperazine-2 -carboxylic acid, 12 mg (0.087 mmole) of HOBt, 21 mg (0.11 mmole) of EDAC, and 22 mg (0.16 mmole) of 2-diethylaminoethylamine after purification by flash chromatography on 16 g of silica gel with 100:5:0.2 CH$_2$Cl$_2$:MeOH: ammonia water provided 45 mg (93%) of an oil.

Mass Spectrum (FAB): m/Z 607 (M+H, 100%), 438 (10%), 324 (8%), 196 (25%). $^1$H NMR (CDCl$_3$, 400 MHz, ppm): δ0.85 (t, 6H), 1.02 (t, 6H), 1.15–1.35 (m, 8H), 1.46 (pentet, 4H), 2.5–2.6 (m, 6H), 2.63 (td, 1H), 2.79 (dd, 1H), 3.0–3.4 (m, 9H), 3.75 (br d, 1H), 3.93 (d, 1H), 7.04 (br s, 1H), 7.08–7.2 (m, 6H), 7.28–7.4 (m, 4H).

EXAMPLE 27

(S)-2-[(4-(N,N-Diethylamino)butyl)aminocarbonyl]-1-[N-(3,5-dimethylphenyl)-N-phenylcarbamoyl]-4-(N,N-di-n-pentylcarbamoyl)piperazine Step A: N-Acetyl-3,5-dimethylaniline To a solution of 15.2 g (125 mmole) of 3,5dimethylaniline in 60 mL of toluene was added 15 g (146 mmole) of acetic anhydride, whereupon the internal temperature rose to 75° C. The mixture was allowed to cool to room temperature and the solvent was removed in vacuo. The residue was dissolved in 150 mL of hot ethyl acetate and the solution allowed to stand for 16 hours. The resulting mixture was cooled at 5° C. for 3 hours and the solid collected by filtration to give 18.43 g (90%) of off-white crystals.

$^1$H NMR (CDCl$_3$, 400 MHz, ppm): δ2.14 (s, 3H), 2.29 (s, 6H), 6.73 (s, 1H), 7.05 (br s, 1H), 7.11 (s, 2H).

Step B: N-(3,5-Dimethylphenyl)aniline

A mixture of 9.6 g (58.8 mmole) of N-acetyl-3,5-dimethylaniline, 8.13 g (58.8 mmole) of potassium carbonate (dried at 155° C. under vacuum), 23 g (147 mmole) of bromobenzene (dried over molecular sieves), and 1.12 g (5.9 mmole) of cuprous iodide was heated in a 175° C. oil bath under a reflux condenser under nitrogen for 18 hours. The mixture was cooled to room temperature and triturated with 1 liter of benzene. The solution was concentrated in vacuo. The residue was treated with 60 mL of EtOH and 7.76 g (118 mmole) of potassium hydroxide and the resulting mixture was heated to reflux for two hours. The mixture was cooled and the solvent removed in vacuo. The residue was taken up in 150 mL of hexanes and 20 mL of EtOAc and the resulting solution was washed with 2×100 mL of 2N aqueous HCl and 60 mL of water. The organic layer was dried over sodium sulfate, filtered and concentrated in vacuo. The residue was purified by flash chromatography on 210 g of silica gel with 2 liters of 3:1 hexanes CH$_2$Cl$_2$ to give 5.5 g (47%) of a light red oil.

$^1$H NMR (CDCl$_3$, 400 MHz, ppm): δ2.24 (s, 6H), 5.60 (br s, 1H), 5.59 (s, 1H), 6.71 (s, 2H), 6.91 (t, 1H), 7.05 (d, 2H), 7.2–7.3 (m, 2H).

Step C: N-(3,5-Dimethylphenyl)-N-phenylcarbamoyl chloride

According to the procedure of Example 15, Step A, 5.5 g (27.9 mmole) of N-(3,5-dimethylphenyl)aniline, 27.9 mL of 1.93M phosgene in toluene and 15 mL of toluene gave 7.15 g (99%) of a red oil.

$^1$H NMR (CDCl$_3$, 400 MHz, ppm): δ2.29 (s, 6H), 6.92 (br s, 3H), 7.2–7.45 (m, 5H).

Step D: (S)-4-(Benzyloxycarbonyl)-1-[N-(3,5-dimethylphenyl)-N-phenylcarbamoyl]-piperazine-2-carboxylic acid A mixture of 800 mg (2.72 mmole) of (S)-4-(benzyloxycarbonyl)piperazine-2-carboxylic acid, 707 mg (2.72 mmole) of N-(3,5-dimethylphenyl)-N-phenylcarbamoyl chloride and 760 mg (5.45 mmole) of triethylamine was stirred in 10 mL of DMF for 48 hours at room temperature. The solution was concentrated in vacuo and the residue purified by flash chromatography on 125 g of silica gel eluting with 1 liter of 100:2 CH$_2$Cl$_2$:MeOH then 800 mL of 100:5:0.2 CH$_2$Cl$_2$:MeOH: HOAc to give 1.32 g of an oil which by $^1$H NMR contained residual DMF and HOAc.

Step E: (S)-1-[N-(3,5-Dimethylphenyl)-N-phenylcarbamoyl]-piperazine-2-(S)-carboxylic acid acetate salt A solution of (S)-1-[N-(3,5-dimethylphenyl)-N-phenylcarbamoyl]-4-(benzyloxycarbonyl)piperazine-2-carboxylic acid (prepared in Step D above) in 9 mL of MeOH was treated with 7 drops of acetic acid and 170 mg of 10% Pd/C. The mixture was stirred under an atmosphere of hydrogen for 4 hours, when an additional 50 mg of 10% Pd/C was added. After stirring under an atmosphere of hydrogen for an additional 2 hours, the mixture was filtered through Celite and the filter cake rinsed with 200 mL of MeOH. The filtrate was concentrated in vacuo to give 228 mg of a white paste which was carried on in Step F below.

Step F: (S)-1-[N-(3,5-Dimethylphenyl)-N-phenylcarbamoyl]-4-(N,N-di-n-pentylcarbamoyl)-piperazine-2-carboxylic acid A mixture of 220 mg (0.53 mmole) of 1-[N-(3,5-dimethylphenyl)-N-phenylcarbamoyl]-piperazine-2-(S)-carboxylic acid acetate salt (from Step E above), 175 mg (0.80 mmole) of N,N-di-n-pentylcarbamoyl chloride and 188 mg (1.86 mmole) of triethylamine in 6 mL of THF and 3 mL of water was stirred at 55° C. for 72 hours. To the mixture was added an additional 6 mL of THF, 175 mg of N,N-di-n-pentylcarbamoyl chloride, and 187 mg of triethylamine and the mixture again heated at 55° C. for 48 hours. To the mixture was added an additional 120 mg N,N-di-n-pentyl-carbamoyl chloride and the reaction mixture heated for an additional 24 hours. The mixture was cooled and was partitioned between 16 mL of 0.5N aqueous HCl and 30 mL of EtOAc. The layers were separated and the aqueous layer extracted with 2×40 mL of EtOAc. The organic layer was dried over magnesium sulfate, filtered and concentrated in Vacuo. The residue was purified by flash chromatography on 68 g of silica gel eluting with 100:4:0.1 CH$_2$Cl$_2$:MeOH: HOAc to give 194 mg (68%) of an oil.

Mass Spectrum (FAB): m/Z 559 (M+Na, 4%), 537 (M+H, 60%), 532 (20%), 492 (M-CO$_2$H, 5%), 341 (M-PhNAr, 15%), 308 (20%), 224 (ArN(CO)Ph, 95%), 196 (45%), 184 ([CH$_3$(Cl$_2$)$_4$]$_2$NCO, 100%). $^1$H NMR (CDCl$_3$, 400 MHz, ppm): δ0.85 (t, 6H), 1.1–1.35 (m, 8H), 1,45 (pentet, 4H), 2.24 (s, 6H), 2.64 (t, 1H), 2.90 (d, 1H), 3.05–3.25 (m, 6H), 3.61 (d, 1H), 3.93 (d, 1H), 4.74 (s, 1H), 6.72 (s, 2H), 6.79 (s, 1H), 7.05–7.15 (m, 3H), 7.29 (t, 2H).

Step G: (S)-2-[(4-(N,N-Diethylamino)butyl)aminocarbonyl]-1-[N-(3,5-dimethylphenyl)-N-phenyl-carbamoyl]-4-(N,N-di-n-pentylcarbamoyl)piperazine According to the procedure of Example 19 above, 40 mg (0.075 mmole) of 1-[N-(3,5-dimethylphenyl)-N-phenylcarbamoyl]-4-(N,N-di-n-pentylcarbamoyl)piperazine-2-carboxylic acid, 12 mg (0.089 mmole) of HOBt, 21 mg (0.112 mmole) of EDAC, and 22 mg (0.15 mmole) of 4-diethylaminobutylamine after purification by flash chromatography on 16 g of silica gel with 100:10:0.2:0.4 C$_2$Cl$_2$:MeOH: ammonia water:water provided 41 mg (84%) of an oil.

Mass Spectrum (FAB): m/Z 663 (M+H, 100%), 466 (M-ArNPh, 3%), 224(ArN(Ph)CO, 25%), 196 (ArNPh, 20%), 184 ([CH$_3$(CH$_2$)$_4$]$_2$NCO, 18%). $^1$H NMR (CDCl$_3$, 400 MHz, ppm): δ0.85 (t, 6H), 1.07 (br t, 6H), 1.1–1.3 (m, 8H), 1.4–1.6 (m, 8H), 2.23 (s, 6H), 2.55–2.75 (m, 6H), 2.75 (td, 1H), 2.84 (dd, 1H), 2.92–3.07 (m, 3H), 3.1–3.35 (m, 5H), 3.68 (d, 1H), 3.93 (d, 1H), 4.47 (s, 1H), 6.72 (s, 2H), 6.79 (s, 1H), 7.08–7.16 (m, 3H), 7.21 (br s, 1H), 7.25–7.33 (m, 2H).

EXAMPLE 28

(S)-1-[N-(3-Chlorophenyl)-N-phenylcarbamoyl]-2-[(3-(N,N-diethylamino)propyl)aminocarbonyl]-4-(N,N-diphenylcarbamoyl)piperazine According to the procedure of Example 19 above, 20 mg (0.036 mmole) of (S)-1-[N-(3-chlorophenyl)-N-phenylcarbamoyl]-4-(N,N-diphenylcarbamoyl)piperazine-2-carboxylic acid, 6 mg (0.041 mmole) of HOBt, 10 mg (0.051 mmole) of EDAC, and 10 mg (0.072 mmole) of 3-diethylaminopropylamine after purification by flash chromatography on 16 g of silica gel with 100:7:0.2 CH$_2$Cl$_2$:MeOH: ammonia water provided 20 mg (83%) of an oil.

Mass Spectrum (FAB): m/Z 667(M+H, 100%), 633 (15%), 230 (25%), 196 (35%). $^1$H NMR (CDCl$_3$, 400 MHz, ppm): δ1.00 (t, 6H), 1.69 (br pentet, 2H), 2.35–2.65 (m, 7H), 2.86 (dd, 1H), 3.02 (br t, 1H), 3.33 (q, 2H), 3.4–3.55 (m, 2H), 4.22 (d, 1H), 4.42 (br s, 1H), 6.95–7.45 (m, 19H), 7.52 (br s, 1H).

EXAMPLE 29

(S)-2-[(3-(N,N-Dimethylamino)propyl)aminocarbonyl]-4-(N,N-di-n-pentylcarbamoyl)-1-(N,N-diphenylcarbamoyl)piperazine According to the procedure of Example 19 above, 40 mg (0.079 mmole) of (S)-1-(N,N-diphenylcarbamoyl-4-(N,N-di-n-pentylcarbamoyl)piperazine-2carboxylic acid, 12 mg (0.087 mmole) of HOBt, 21 mg (0.11 mmole) of EDAC, and 20 mg (0.16 mmole) of 3-dimethylaminopropylamine after purification by flash chromatography on 16 g of silica gel with 100:7:0.2 CH$_2$Cl$_2$:MeOH: ammonia water provided 33 mg (70%) of an oil.

Mass Spectrum (FAB): m/Z 593 (M+H,100%), 196 (15%). $^1$H NMR (CDCl$_3$, 400 MHz, ppm): δ0.82 (t, 6H), 1.1–1.3 (m, 8H), 1.44 (pentet, 4H), 1.64 (pentet, 2H), 2.20 (s, 6H), 2.25–2.4 (m, 2H), 2.65–2.8 (m, 2H), 3.0–3.35 (m, 8H), 3.73 (d, 1H), 3.88 (d, 1H), 4.47 (br s, 1H), 7.05–7.15 (m, 6H), 7.27–7.35 (m, 4H), 7.64 (br t, 1H).

EXAMPLE 30

(S)-2-[(3-(N,N-Diethylamino)propyl)aminocarbonyl]-1-[N-(3,5-dimethylphenyl)-N-phenylcarbamoyl]-4-(N,N-di-n-pentylcarbamoyl)piperazine According to the procedure of Example 19 above, 41 mg (0.076 mmole) of (S)-1-[N-(3,5-dimethyl-phenyl)-N-phenylcarbamoyl]-4-(N,N-di-n-pentylcarbamoyl)piperazine-2-carboxylic acid, 12 mg (0.092 mmole) of HOBt, 22 mg (0.115 mmole) of EDAC, and 21 mg (0.153 mmole) of 4-diethylaminopropylamine after purification by flash chromatography on 16 g of silica gel with 100:10:0.3:0.4 CH$_2$Cl$_2$:MeOH: ammonia water:water provided 44 mg (88%) of an oil.

Mass Spectrum (FAB): m/Z 649 (M+H, 100%), 224 (ArN(Ph)CO, 25%), 184 ([CH$_3$(CH$_2$)$_4$]$_2$NCO, 20%). $^1$H NMR (CDCl$_3$, 400 MHz, ppm): δ0.86 (t, 6H), 0. 99 (br s, 6H), 1.15–1.3 (m, 8H), 1.45 (pentet, 4H), 2.23 (s, 6H), 2.4–2.55 (m, 6H), 2.69 (br t, 1H), 2.82 (br d, 1H), 3.0–3.4 (m, 10H), 3.71 (br d, 1H), 3.90 (d, 1H), 4.50 (s, 1H), 6.71 (br s, 2H), 6.78 (s, 1H), 7.05–7.15 (m,3H), 7.27–7.35 (m, 3H).

EXAMPLE 31

(S)-2-[(2-(N,N-Dimethylamino)ethyl)aminocarbonyl]-4-(N,N-di-n-pentylcarbamoyl)-1-(N,N-diphenylcarbamoyl)piperazine According to the procedure of Example 19 above, 33 mg (0.065 mmole) of (S)-1-(N,N-diphenylcarbamoyl)-4-(N,N-di-n-pentylcarbamoyl)piperazine-2-carboxylic acid, 10 mg (0.071 mmole) of HOBt, 17 mg (0.091 mmole) of EDAC, and 14 mg (0.13 mmole) of 2dimethylaminoethylamine after purification by flash chromatography on 16 g of silica gel with 100:7:0.2 $CH_2Cl_2$:MeOH: ammonia water provided 33 mg (87%) of an oil.

Mass Spectrum (FAB): m/Z 580 (~M+H, 100%), 196 (20%). $^1$H NMR (CDCl$_3$, 400 MHz, ppm): δ0.85 (t, 6H), 1.12–1.33 (m, 8H), 1.45 (pentet, 4H), 2.22 (s, 6H), 2.39 (t, 2H), 2.67 (td, 1H), 2.81 (dd, 1H), 3.0–3.1 (m, 3H), 3.15–3.40 (m, 5H), 3.72 (d, 1H), 3.94 (d, 1H), 4.53 (s, 1H), 7.06 (br t, 1H), 7.07–7.15 (m, 6H), 7.30 (t, 4H).

EXAMPLE 32

1,4-bis[N-(3-Chlorophenyl)-N-phenylcarbamoyl]-2,5trans-dimethylpiperazine

A mixture of 1.33 g (5 mmole) of 3-chlorodiphenylcarbamoyl chloride and 650 mg (5 mmole) of DIEA in 20 mL of methylene chloride was treated with 286 mg (2.5 mmole) of trans-2,5-dimethylpiperazine and the mixture was stirred for 54 hr. The solution was treated with 20 mL of water, the layers were separated and the organic layer was washed with 10 mL each of 2N HCl (twice), 5% aqueous sodium bicarbonate, water, and saturated sodium chloride. The organic phase was dried over magnesium sulfate and the solvent was removed in vacuo. The residue was treated with isopropyl ether to give 712 mg (50%) of a white solid, mp 239°–241° C., homogeneous by TLC (200:1:19 $CH_2Cl_2$:ammonia water: EtOH).

Mass Spectrum (FAB): m/Z 573(M+H, 100%). Analysis. ($C_{32}H_{30}N_4O_2Cl_2$): Calculated: C, 67.01; H, 5.27; N, 9.77. Found: C, 67.07; H, 5.16; N, 9.45.

EXAMPLE 33

(S)-4-(Dipentylcarbamoyl)-1-(diphenylcarbamoyl)-2-(hydroxymethyl)piperazine 1.24 g (2.44 mmole) of (S)-4-(dipentylcarbamoyl)-1-(diphenylcarbamoyl)piperazine-2-carboxylic acid dissolved in 6 ml of THF was cooled to 0° C. in an ice bath. To this 9 ml (9 mmole) of 1.0M borane solution in THF was slowly added during a 15 min. period. The resulting mixture was stirred for 24 hr at 25°. The excess hydride was destroyed carefully with 20 ml of a 1:1 mixture of THF and water. The aqueous phase was saturated with anhydrous potassium carbonate. The THF layer was separated and aqueous layer was extracted with ether. The combined organic phase was dried over magnesium sulfate. The solvents were removed on a rotary evaporator to yield 1.18 g (98%) of (S)-4-(dipentylcarbamoyl)-1-(diphenylcarbamoyl)-2-(hydroxymethyl)piperazine as a white solid, mp 133°–134°.

Mass spectrum (FAB): m/e 495 Analysis ($C_{29}H_{42}N_4O_3$) Calculated: C, 70.41; H, 8.56; N, 11.33 Found: C, 70.20; H, 8.68; N, 11.34

EXAMPLE 34

(S)-1-(Diphenylcarbamoyl)-4-N-pentyl-N-[2-(1H-tetrazol-5-yl]biphenyl-4-yl)-methyl]carbamoyl]piperazine-2-carboxylic acid Step A: N-Pentyl-N-[2-(1-trityltetrazol-5-yl)biphenyl-4-yl)methyl]amine A solution of 10.0 g (17.9 mmole) of 1-[2-(1-trityltetrazol-5-yl)biphenyl-4-yl)methyl]bromide and 3 ml (21.5 mmole) of triethylamine in 100 ml of DMF was treated over 5 min with 8 g (91.8 mmole) of pentylamine with stirring, as the solution was stirred for 16 hr at 25°. The solution was concentrated in vacuo at 55° and the residue was redissolved in 100 ml of dichloromethane which was washed with 50 ml of 0.5M citric acid with 100 ml of 0.25M citric acid. After concentration the residue was dissolved in 75 ml of ethyl acetate at 45°. Crystallization gave 9.15 g (90%) of white crystalline solid which was homogeneous by the (silica, ethyl acetate, $R_f$=0.45).

Mass Spectrum (FAB): 570 (M+L) $^1$H NMR (CDCl$_3$, 400 MHz, ppm):δ0.80 (t,3H)1.20 (m,4H), 1.82 (m,2H), 2.68 (m,2H), 3.97 (s,2H), 6.99 (d, 6H), 7.15 (d, 2H), 7.68 (m, 8H), 7.34 (m, 4H), 7.45 (m, 2H), 7.93 (m, 1H).

Step B: N-Pentyl-N-[2-(1-trityltriazol-5-yl)biphenyl-4-yl)methyl]carbamoyl chloride A solution of 3.07 (5.45 mmole) of N-Pentyl-N-[2-(1-trityltetrazol-5-yl)biphenyl-4-yl)methyl]amine in 35 ml of toluene was stirred rapidly at −5° with 9.00 ml (24.9 mmole) of 2.77N sodium hydroxide, and 8.00 ml (15.44 mmole) of 1.93M phosgene in toluene was added dropwise over 15 min. The mixture containing toluene layer was filtered and the excess phosgene was removed by displacement with nitrogen for 15 min. The resulting solution was concentrated to 1.69 g (50%) of colorless oil which was largely homogeneous by tlc (4:1 hexaneethyl acetate, $R_f$=0.40, no starting amine).

IR (neat)(cm−$^1$): 1740 $^1$H NMR (CDCl3, 400 MHz, ppm): δ0.87 (m, 3H), 1.19 (m,2H), 1.29 (m, 2H), 1.56 (m, 2H), 3.17 (m, 2H), 4.45 and 4.56 (d, 2H), 6.88 (d, 6H), 6.99(m, 2H), 7.09–7.19(m, 2H), 7.22–7.28(m, 6H), 7.30–7.38 (m, 4H), 7.47 (m, 2H), 7.96 (m, 1H).

Step C: (S)-1-(Diphenylcarbamoyl)-4-[N-pentyl-N-[2-(1H-tetrazol-5-yl)biphenyl-4-yl)methyl]carbamoyl]piperazine-2-carboxylic acid A solution of 113 mg (0.29 mmole) (S)-1-(diphenylcarbamoyl)piperazine-2-carboxylic acid acetate salt was mixed with 1.5 ml of DMF and treated with 129 mg (1.00 mmole) of diisopropylethylamine, and diisopropylethylamine a solution of 169 mg (0.27 mmole) of N-pentyl-N-[2-(1-trityltetrazol-5-yl)biphenyl-4-yl)methyl]carbamoyl chloride in 0.5 ml of DMF was added dropwise over 1 min. The mixture was stirred at 25° for 16 hr, and after concentrating in vacuo the resulting paste was dissolved in 2 ml of methanol which was treated with 8 drops of conc. hydrochloric acid. After 2 hr at 25° the clear solution was concentrated in vacuo, and the residue was dissolved in methanol which was treated with 1.5 ml of 2.77N sodium hydroxide. The solution was stirred for 16 hr at 25° and after concentrating in vacuo, the residue was triturated with 10 ml of 0.1N hydrochloric acid. The solid was filtered and dried and was then applied to four 20 cm×20 cm×2 mm silica gel plates which were eluated with 80-chloroform: 20-methanol: 2-concentrated ammonia. The band with $R_f$0.17 to 0.28 was washed with 150 ml of methanol which was concentrated in vacuo. The residue was dissolved in 30 ml. of dichloromethane which was washed with 10 ml of 0.5M citric acid. Concentration gave 82 mg (42%) of white solid which was homogeneous by the (silica gel, 80-chloroform: 20-methanol: 2-concentrated ammonia, r$_f$=0.25).

Mass Spectrum (FAB):m/e 673 (M+1) $^1$HNMR (CDCl$_3$, 400 MHz, ppm): δ0.85 (t, 3H), 1.22 (m, 2H), 1.28 (m, 2H), 1.54 (m, 2H), 2.74 (t, 1H), 2.93 (d, 1H), 3.01 (m, 1H), 3.16 (m, 1H), 3.34 (m, 1H), 3.51 (d, 1H), 3.63 (d, 1H), 3.98 (d, 1H), 4.07 (d, 1H), 4.17 (d, 1H), 4.64 (s, 1H), 7.06 (m, 6H), 7.09–7.19 (m, 4H), 7.23–7.29 (m, 4H), 7.42 (d, 1H), 7.49–7.61 (d of t, 2H), 8.04 (d, 1H).

EXAMPLE 35

(S)-4-(Dipentylcarbamoyl)-1-[N-pentyl-N-[2-(1H-tetrazol-5-yl)biphenyl-4-yl)methyl]carbamoyl]piperazine-2-carboxylic acid Step A: (S)-4-(Benzyloxycarbonyl)-1-(tert-butoxycarbonyl-piperazine-2-carboxylic acid A solution of 3.33 g (12.6 mmole) of (S)-4-(benzyloxycarbonyl)piperazine-2-carboxylic acid in 37 ml of water was treated with 12.6 ml (12.6 mmole) of 1N sodium hydroxide and 50 ml of tert-butyl alcohol. The clear solution was cooled to 10°–15° and 2.82 g (12.92 mmole) of di-tert butyl dicarbonate was added in one portion with stirring. After allowing to warm to 25° over 1 hr, the clear solution was diluted with 300 ml of water and was extracted with 3×250 ml of pentane. The aqueous solution was cooled over ice and was acidified to pH 2.5 with a concentrated solution of potassium bisulfate. After extraction with 2×125 ml of ethyl acetate which was dried over anhydrous magnesium sulfate, concentration in vacuo gave 4.48 g (98%) of viscous oil which was homogeneous by the (silica gel, ethyl acetate, R$_f$=0.3–0.6).

Mass Spectrum (FAB): m/e 409 (m+2Na), 387 (M+Na), 365 (M+1), 265 (loss of Boc). $^1$HNMR (CDCl$_3$, 200MHz, ppm): δ1.47 (br.s, 9H), 2.85–3.05 (br.m, 1H), 3.05–3.30 (m,2H), 3.8–4.0 (m, 1H), 4.0–4.15 (m, 1H), 4.6–4.7 (m, 1H), 4.7–5.9 (d, 1H), 5.14 (d, 2H), 7.35 (s, 5H).

Step B: (S)-1-(tert-Butyloxycarbonyl)piperazine-2-carboxylic acid

A solution of 4.00 g (10.98 mmole) of (S)-4-(benzyloxycarbonyl)-1-(tert-butyloxycarbonyl)-piperazine-2-carboxylic acid in 40 ml of methanol was hydrogenated over 1.0 g of 10% pd/c with rocking at 25° under 40 psi of hydrogen for 16 hr. The mixture was filtered and the cake was washed with a mixture of 100 ml of dichloromethane, 50 ml of methanol and 1.0 g of diisopropylethyl amine. Concentration in vacuo followed by Pumping in vacuo for 2 hr left 2.39 g (95%) of white solid which was homogeneous by tlc (silica gel, 1:1:1:1 ethyl acetate:n-butanol:acetic acid:water, R$_f$=0.70).

Mass Spectrum (FAB): m/e 275 (M+2Na), 253 (M+Na), 231(M+1).

Step C: (S)-1-(tert-Butyloxycarbonyl)-4-(dipentylcarbamoyl)piperazine-2-carboxylic acid A partial solution of 1.32 g (5.74 mmole) of (S)-1-(tert-butyloxycarbonyl)piperazine-2-carboxylic acid in 25 ml of dried DMF was treated dropwise over 5 min with 1.48 g (11.47 mmole of diisopropylethyl amine at 25° under nitrogen with stirring. The clear solution which resulted was treated dropwise over 15 min with a solution of 1.26 g (5.74 mmole) of dipentylcarbamoyl chloride in 5 ml of DMF and the mixture was stirred under nitrogen at 25° for 16 hr. The solution was concentrated in vacuo and the residue was dissolved in 100 ml of dichloromethane which was extracted with 2×100 ml of 0.5M citric acid and 2×25 ml of water. Without drying, the solution was concentrated in vacuo to 1.85g (78%) of medium yellow oil which was homogeneous by the (silica gel, 1:1:1:1 ethylacetate: n-butanol: acetic acid: water, R$_f$=0.50).

Mass Spectrum (FAB): m/e 414 (M+1), 358 (loss of butyl) $^1$H NMR (CDCl$_3$, 400 MHz, ppm): δ0.86 (t, 6H), 1.20 (m, 4H), 1.27 (m, 4H), 2.46 (m, 13H), 2.82 (m, 1H), 3.10 (m, 4H), 3.16 (m, 2H), 3.42 (d of d, 1H), 3.84 (d of d, 1H), 4.04 (d, 1H), 4.61–4.77 (d, 1H).

Step D: (S)-4-(Dipentylcarbamoyl)piperazine-2-carboxylic acid

A solution of 1.85 g (4.47 mmole) of (S)-1-(tert-butyloxycarbonyl)-4-(dipentylcarbamoyl)-piperazine-2-carboxylic acid in 20 ml of trufloroacetic acid was stirred at 25° for 2 hr. The excess solvent was concentrated in vacuo, and the residue was dissolved in 150 ml of ethyl acetate which was extracted with 2×75 ml of 5% sodium bicarbonate. The aqueous layers were neutralized to pH 7.0 with 6N hydrochloric acid and were extracted with 2×50 ml of dichloromethane which was concentrated wothout drying to 0.732 g (52%) of oil which was homogeneous by the (silica gel, 5:1:1:1 ethyl acetate: n-butanol: acetic acid: water, R=0.38).

Mass Spectrum (FAB): m/e 314 (M+1) $^1$H NMR (CDCl$_3$, 400 MHz, ppm): δ0.87 (t, 6H), 1.19 (m, 4H), 1.29 (m, 4H), 1.48 (m, 4H), 3.12 (brm, 8H), 3.35 (brm, 1H), 3.53 (brm, 1H), 3.90 (brm, 1H).

Step E: (S)-4-(Dipentylcarbamoyl)-1-{N-pentyl-N-[2-(1H-tetrazol-5-yl)biphenyl-4-yl)methyl]carbamoyl]piperazine-2-carboxylic acid A solution of 224 mg (0.71 mmole) of (S)-4-(dipentylcarbamoyl)piperazine-2-carboxylic acid in 3 ml of DMF was treated with 310 mg (2.48 mmole) of diisopropylethylamine to give a clear solution. A solution of 445 mg (0.71 mmole) of N-pentyl-N-[2-(1-trityltriazol-5-yl)methyl]carbamoyl chloride in 1 ml of DMF was added dropwise over 5 min at 25° to the stirred solution. After stirring for 16 hr, the solution was removed in vacuo. The residue was dissolved in 10 ml of methanol which was treated with 8 drops of conc'd hydrochloric acid. The solution was stirred at r.t. for 16 hr. The solution was concentrated in vacuo and the residue was dissolved in 40 ml of dichloromethane which was washed with 15 ml of 0.5M citric acid. After concentration in vacuo to a gum, the crude product (723 mg) was applied to eight 20 cm×20 cm×2 mm. Analtech silica gel GF plates which were eluted with 80-chloroform: 20-methanol: 2-conc'd ammomia. The bands from R$_f$=0.24 to 0.37 from each plate were combined and washed with 300 ml of the 80:20:2 solvent which was concentrated in vacuo to a gum. The product was partitioned between 40 ml of dichloromethane and 20 ml of 1N hydrochloric acid. Concentration of the dichloromethane without drying gave 170 mg (36%) of a pale tan foam which was homogeneous by the (80-chloroform: 20-methanol: 2-conc'd ammonia, R$_f$=0.40).

Mass Spectrum (FAB): m/e 672.7 (M+Na) $^1$H NMR (CDCl$_3$, 400 MHz, ppm): δ0.82 (t, 6H), 0.90 (t,3H), 1.05–1.38 (m, 12H), 1.42–1.50 (m, 4H), 1.60–1.72 (t of t, 2H), 2.7 9–2.85 (m, 1H), 2.95 (d of d, 1H), 3.08–3.17 (m, 2H), 3.17–3.26 (m, 4H), 3.27–3.36 (m, 2H), 3.45 (d, 1H) , 3.87 (d, 1H), 4.17 (d, 1H), 4.24 (brs, 1H), 4.42 (d, 1H), 7.11 (d, 2H), 7.24 (m, 1H), 7.41 (d, 1H), 7.48–7.59 (m, 3H), 8.11 (d, 1H).

EXAMPLE 36

(S)-4-(Diphenylcarbamoyl)-1-{N-pentyl-N-[2-(1H-tetrazol-5-yl)biphenyl-4-yl)methyl]carbamoyl}piperazine-2-carboxylic acid A solution of 161 mg (0.42 mmole) of (S)-4-(diphenyl-carbamoyl-piperazine-2-carboxylic acid acetate salt has mixed with 1.5 ml of DMF and treated with 178 mg (1.38 mmole) of diisopropylethylamine, and a solution of 332mg (0.53 mmole)of N-pentyl-N-[2-(1-trityltetrazol-5-yl)biphenyl-4-yl)methyl]carbamoyl chloride in 0.5 ml of DFM was added dropwise over 1 min. The mixture was stirred at 25° for 16 hr, and after concentrating in vacuo the resulting paste was dissolved in 2 ml of methanol which was treated with 8 drops of conc'd hydrochloric acid. After 2 hr at 25°, the clear solution was concentrated in vacuo, and the residue was dissolved in methanol which was treated with 1.5 ml of 2.77N sodium hydroxide. The solution was stirred for 16 hr at 25°, and after concentrating in vacuo, the residue was triturated with 10 ml of of 0.1N hydrochloric acid. The solid was filtered and dried and was then applied to four 20 cm×20 cm×2 mm silica gel plates which were eluted with 80-chloroform: 20-methanol: 2-concentrated ammonia. The band with $R_f$ 0.20–0.33 was washed with 150 ml of methanol which was concentrated in vacuo. The residue was dissolved in 30 ml of dichloromethane which was washed with 10 ml of 0.5M citric acid. Concentration gave 112 mg (40%) of white solid which was homogeneous by the (silica gel, 80-chloroform: 20-methanol: 2-concentrated ammonia, $R_f$=0.25).

Mass Spectrum (FAB): m/e 695 (M+Na), 673 (M+1) $^1$H NMR (CDCl$_3$, 400 MHz, ppm): δ0.87 (t,3H), 1.23 (m, 2H), 1.29 (m, 2H), 1.59 (m, 2H), 2.92 (m, 2H), 3.03 (m, 1H), 3.19 (m, 2H), 3.26 (d, 1H), 3.77 (d, 1H), 4.17 (s, 2H), 4.20 (d, 1H), 4.35 (d, 1H), 7.04 (m, 4H), 7.08 (m, 4H), 7.17 (d, 2H), 7.24 (m, 4H), 7.38 (d, 1H), 7.46–7.57 (d of t, 2H), 8.00 (d, 1H).

EXAMPLE 37

(S)-4-(Dipentylcarbamoyl)-1-(diphenylcarbamoyl)piperzine-2(3-morpholinopropyl)carboxamide To a solution of 310 mg (0.61 mmole) of (S)-4-(dipentylcarbamoyl)-1-(diphemylcarbamoyl)piperazine-2-carboxylic acid in 6 ml of tetrahydrofuran are added 98 mg (0.64 mmole) of 1-hydroxybenzotriazole hydrate (HOBT) and 141 mg (0.68 mmole) of N,N$^1$-dicyclohexylcarbodiimide (DCC). After an half hour at r.t. under stirring, 106 mg (0.73 mmole) of 3-aminopropylmorpholine are dropwise added and the reaction mixture kept overnight under stirring. After filteration of the precipitated N,N-dicyclohexylurea, the residual solution was concentrated in vacuo and then shaken with dichloromethane. The organic phase was extracted with water, saturated sodium bicarbonate, 1N HCl and saturated sodium chloride. After drying over magnesium sulfate the dichloromethane was removed in vacuo to yield 278 mg (72%) of glassy solid; satisfactory purity by tlc (5:2:1 Isoamyl alcohol: acetone: water, $R_f$=0.85).

Mass (FAB): m/e 635 (M+1) $^1$H NMR (CDCl$_3$, 400 MHz, ppm): δ0.85 (t, 6H), 1.17 (m, 4H), 1.26 (m, 4H), 1.41 (m, 4H), 1.59 (m, 4H), 1.64–1.72 (m, 2H), 2.48 (t, 1H), 2.89 (m, 2H), 3.06 (t, 6H), 3.30–3.55 (m, 8H), 3.80 (t, 2H), 3.91 (d of d, 1H), 4.20 (t, 1H), 4.29 (t, 1H), 4.40 (t, 1H), 7.15 (t, 2H), 7.23–7.34 (m, 8H), 8.11 (s, 1H).

EXAMPLE 38

Typical Pharmaceutical Compositions Containing a Compound of the Invention

A: Dry Filled Capsules Containing 50 mg of Active

| Ingredient | Amount per capsule (mg) |
|---|---|
| Active ingredient | 50 |
| Lactose | 149 |
| Magnesium stearate | 1 |
| Capsule (size No. 1) | 200 |

The active ingredient can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain the active ingredient (25 mg), pregelatinized starch USP (82 mg), microcrystalline cellulose (82 mg) and magnesium stearate (1 mg).

C: Suppository

Typical suppository formulations for rectal administration contain the active ingredient (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol.

D: Injection

A typical injectible formulation contains the acting ingredient sodium phosphate dibasic anhydrous (11.4 mg), benzyl alcohol (0.01 ml) and water for injection (1.0 ml). While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of structural formula:

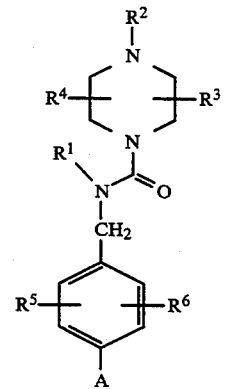

or a pharmaceutically acceptable salt thereof, wherein:
A is selected from:

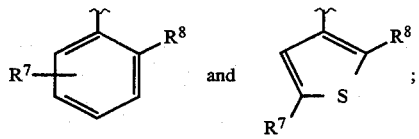

$R^1$ is selected from the group consisting of:
1) H,
2) $C_{1-8}$ alkyl,
3) $C_{3-7}$ cycloalkyl,
4) phenyl, either unsubstituted or substituted with one or two substituents selected from:
   a) $C_{1-4}$ alkyl,
   b) -halo,
   c) —OH
   d) —$CF_3$
   e) —$NH_2$,
   f) —NH($C_{1-4}$ alkyl),
   g) —N($C_{1-4}$ alkyl)$_2$,
   h) —$CO_2H$,
   i) —$CO_2$($C_{1-4}$ alkyl), and
   j) —$C_{1-4}$ alkoxy; or
5) $C_{1-4}$ alkyl-aryl, wherein the aryl is phenyl or naphthyl, either unsubstituted or substituted with one or two substituents selected from:
   a) —$C_{1-4}$ alkyl,
   b) -halo,
   c) —OH,
   d) —$CF_3$,
   e) —$NH_2$,
   f) —NH($C_{1-4}$ alkyl),
   g) —N($C_{1-4}$ alkyl)$_2$,
   h) —$CO_2H$,
   i) —$CO_2$($C_{1-4}$ alkyl), and
   j) —$C_{1-4}$ alkoxy;

$R^2$ is selected from the group consisting of:
1) —$C_{1-6}$ alkyl,
2) —$CH_2$-aryl, wherein aryl is as defined in $R^1$,
3) —$CH_2$—$C_{3-7}$ cycloalkyl,
4) —$CO_2R^{2a}$, wherein $R^{2a}$ is as defined below,
5) —CON($R^{2a}R^{2b}$), wherein $R^{2a}$ and $R^{2b}$ are as defined below,
6) —$SO_2N(R^{2a}R^{2b})$, wherein $R^{2a}$ and $R^{2b}$ are as defined below,
7) -aryl, wherein aryl is as defined in $R^1$,
8) —CO-aryl, wherein aryl is as defined in $R^1$, and
9) —CO—$C_{1-4}$ alkyl;

$R^{2a}$ and $R^{2b}$ are independently selected from the group consisting of:
1) hydrogen,
2) —$C_{1-8}$ alkyl,
3) —$C_{1-8}$ alkyl-NH($C_{1-8}$ alkyl),
4) —$C_{1-8}$ alkyl-N($C_{1-8}$ alkyl)$_2$,
5) -aryl, wherein aryl is as defined in $R^1$,
6) —$CH_2$-aryl wherein aryl is as defined in $R^1$, or
7) wherein —$NR^{2a}R^{2b}$ may formula heterocyclic ring of the form —N($CH_2CH_2$)$_2$L, wherein L is selected from the group consisting of O, S, N—$C_{1-4}$ alkyl, N-aryl, wherein aryl is as defined in $R^1$, and N—CO—$C_{1-4}$ alkyl;

$R^3$ is selected from the group consisting of:
1) —$CO_2R^{2a}$, wherein $R^{2a}$ is as defined above,
2) —CON($R^{2a}R^{2b}$), wherein $R^{2a}$ and $R^{2b}$ are as defined above,
3) —$CH_2S$—$C_{1-4}$alkyl, and
4) —$CH_2O$—$C_{1-4}$alkyl;

$R^4$ is independently selected from:
1) —H,
2) —$C_{1-6}$alkyl, and
3) —$R^3$;

$R^5$ is selected from the group consisting of:
1) hydrogen,
2) —$C_{1-6}$alkyl,
3) —$C_{2-6}$alkenyl,
4) —$C_{2-4}$alkynyl,
5) halo,
6) —O—$C_{1-4}$alkyl,
7) —$CF_3$,
8) —CN, and
9) —$CH_2O$—$C_{1-4}$alkyl, $R^6$ is independently selected from:
1) H, and
2) $R^5$;

$R^7$ is selected from the group consisting of:
1) —$C_{1-6}$alkyl
2) —$C_{2-6}$alkenyl,
3) —$C_{2-4}$alkynyl,
4) halo,
5) aryl, wherein aryl is as defined in $R^1$,
6) $CH_2$-aryl, wherein aryl is as defined in $R^1$,
7) —O—$C_{1-4}$alkyl,
8) —$CF_3$,
9) —CN, and
10) —$CH_2O$—$C_{1-4}$alkyl;

$R^8$ is selected from the group consisting of:
1) —$CO_2R^9$, wherein $R^9$ is hydrogen or $C_6$alkyl,
2) 1H-tetrazol-5-yl.
3) —$CONHSO_2R^{10}$, wherein $R^{10}$ is selected from:
   a) $C_{1-6}$ alkyl,
   b) —$C_{1-6}$ alkoxy,
   c) aryl, wherein aryl is as defined in $R^1$,
   d) —$CH_2$aryl, wherein aryl is as defined in $R^1$, and
   e) CH(aryl)$_2$,
4) —$SO_2NHR^{10}$,
5) —$NHSO_2R^{10}$,
6) —$SO_2NHCOR^{10}$,
7) —$NHSO_2CF_3$, and
8) —$SO_2NHCO_2R^{10}$.

2. The compound of claim 1 of structural formula:

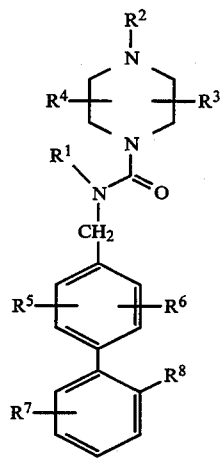

or a pharmaceutically acceptable salt thereof.

3. The compound of claim 1 of structural formula:

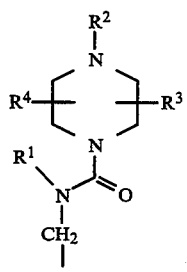

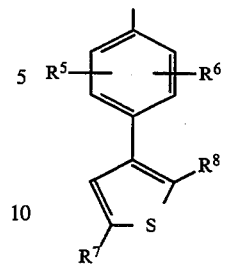

or a pharmaceutically acceptable salt thereof.

4. The compound of claim 1 which is selected from the group consisting of:
1) (S)-1-(diphenylcarbamoyl)-4-N-pentyl-N-[2-(1H-tetrazol-5-yl]biphenyl-4-yl)-methyl]carbamoyl]-piperazine-2-carboxylic acid;
2) (S)-4-(dipentylcarbamoyl)-1-[N-pentyl-N-[2-(1H-tetrazol-5-yl)biphenyl-4-yl)methyl]carbamoyl]-piperazine-2-carboxylic acid;
3) (S)-4-(diphenylcarbamoyl)-1-{N-pentyl-N-[2-(1H-tetrazol-5-yl)biphenyl-4-yl)methyl]carbamoyl}-piperazine-2-carboxylic acid;
4) (S)-1-(diphenylcarbamoyl)-4-{N-pentyl-N-[2-(1H-tetrazol-5-yl]-5-(propyl)-biphenyl-4-yl)-methyl]-carbamoyl}piperazine-2-carboxylic acid; and
5) (S)-1-(diphenylcarbamoyl)-4-{N-pentyl-N-[2-(1H-tetrazol-5-yl]-5-propyl-3-thienyl)phenyl]-methyl]-carbamoyl}-piperazine-2-carboxylic acid.

5. A pharmaceutical composition comprising a pharmaceutically acceptable carrier and an effective amount of the compound of claim 1.

* * * * *